(12) United States Patent
Chorvat et al.

(10) Patent No.: US 6,326,368 B1
(45) Date of Patent: Dec. 4, 2001

(54) ARYLOXY- AND ARYLTHIOSUBSTITUTED PYRIMIDINES AND TRIAZINES AND DERIVATIVES THEREOF

(75) Inventors: Robert John Chorvat, West Chester, PA (US); Parthasarathi Rajagopalan, Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 08/816,706

(22) Filed: Mar. 13, 1997

Related U.S. Application Data

(60) Provisional application No. 60/014,213, filed on Mar. 27, 1996.

(51) Int. Cl.$^7$ ..................... C07D 251/22; C07D 251/30; C07D 413/04; A61K 31/53
(52) U.S. Cl. .................... 514/236.2; 514/227.8; 514/232.2; 514/241; 514/245; 514/217.05; 514/222.5; 514/228.2; 514/229.8; 544/5; 544/8; 544/60; 544/208; 544/209; 544/210; 544/211; 544/212; 544/219; 544/113; 544/83; 544/35; 544/102; 540/598
(58) Field of Search ..................... 544/208, 209, 544/210, 211, 212, 219, 113, 83, 60, 8, 5; 514/227.8, 232.2, 236.2, 241, 245, 217.05, 222.5, 228.2; 540/598

(56) References Cited

U.S. PATENT DOCUMENTS

| | | | |
|---|---|---|---|
| 3,843,650 | * 10/1974 | Pews et al. ........................ 260/248 |
| 3,950,306 | * 4/1976 | Pews et al. .................. 260/45.8 NT |
| 4,039,538 | * 8/1977 | Klinkenberg et al. ............... 544/219 |
| 4,427,437 | 1/1984 | Serban et al. ........................ 71/92 |
| 4,460,588 | 7/1984 | Serban et al. ........................ 424/251 |
| 4,889,788 | * 12/1989 | Stahlhofen et al. ................. 430/191 |
| 4,914,098 | 4/1990 | Boger et al. ........................ 514/274 |
| 4,990,429 | * 2/1991 | Stahhofen et al. ................. 430/325 |
| 5,062,882 | 11/1991 | Newton et al. ........................ 71/93 |
| 5,185,027 | 2/1993 | Vogelbacher et al. .............. 504/219 |
| 5,281,707 | 1/1994 | Fuso et al. ........................ 544/212 |
| 5,449,777 | 9/1995 | Pitteloud ............................ 544/208 |

OTHER PUBLICATIONS

J. Rivier et al., *Proc. Natl. Acad. Sci.* (USA), 80:4851 (1983).
W. Vale et al., *Science*, 213:1394 (1981).
W. Vale et al., *Rec. Prog. Horm. Res.*, 39:245 (1983).
G.F. Koob, *Persp. Behav. Med.*, 2:39 (1985).
E.B. DeSouza et al., *J. Neurosci.*, 5:3189 (1985).
J.E. Blalock, *Physiological Reviews*, 69:1 (1989).
J.E. Morley, *Life Sci.*, 41:527 (1987).
E.B. DeSouza, *Hosp. Practice*, 23:59 (1988).
C.B. Nemeroff et al., *Science*, 226:1342 (1984).
C.M. Banki et al., *Am. J. Psychiatry*, 144:873 (1987).
R.D. France et al., *Biol. Psychiatry*, 23:86 (1988).
M. Arato et al., *Biol. Psychiatry*, 25:355 (1989).
C.B. Nemeroff et al., *Arch. Gen. Psychiatry*, 45:577 (1988).
P.W. Gold et al., *Am. J. Psychiatry*, 141:619 (1984).
F. Holsboer et al., *Psychoneuroendocrinology*, 9:147 (1984).
P.W. Gold et al., *New Eng. J. Med.*, 314:1129 (1986).
R.M. Sapolsky, *Arch. Gen. Psychiatry*, 46:1047 (1989).
Grigoriadis et al., *Neuropsychopharmacology*, 2:53 (1989).
D.R. Britton et al., *Life Sci.*, 31:363 (1982).
C.W. Berridge & A.J. Dunn, *Regul. Peptides*, 16:83 (1986).
C.W. Berridge & A.J. Dunn, *Horm. Behav.*, 21:393 (1987).
*Brain Research Reviews*, 15:71 (1990).
K.T. Britton et al., *Psychopharmacology*, 86:170 (1985).
N.R. Swerdlow et al., *Psychopharmacology*, 88:147 (1986).
K.T. Britton et al., *Psychopharmacology*, 94:306 (1988).
G.F. Koob & K.T. Britton, *Corticotropin–Releasing Factor: Basic & Clinical Studies of a Neuropeptide*, E.B. DeSouza & C.B. Nemeroff, CRC Press, p. 221 (1990).
*Remington's Pharmaceutical Sciences*, 17$^{th}$ ed., Mack Pub. Co., Easton, PA, p. 1418 (1985).
*Helv. Chim. Acta.*, 33, 1365 (1950).
Albert, Brown & Wood, *J. Chem. Soc.*, 3832 (1954).
Lowry et al., *J. Biol. Chem.*, 193:265 (1951).
E.B. DeSouza, *J. Neurosci.*, 7:88 (1987).
Munson & Rodbard, *Anal. Biochem.*, 107:220 (1980).

\* cited by examiner

*Primary Examiner*—John M. Ford
(74) *Attorney, Agent, or Firm*—Gerald J. Boudreaux; Kenneth B. Rubin; Kalim S. Fuzail

(57) ABSTRACT

The present invention provides novel compounds, and pharmaceutical compositions thereof, and methods of using same in the treatment of affective disorders, anxiety, depression, post-traumatic stress disorders, eating disorders, supranuclear palsey, irritable bowel syndrome, immune supression, Alzheimer's disease, gastrointestinal diseases, anorexia nervosa, drug and alcohol withdrawal symptoms, drug addiction, inflammatory disorders, or fertility problems. The novel compounds provided by this invention are those of formula:

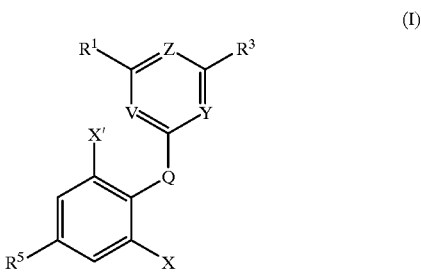

(I)

wherein $R^1$, $R^3$, $R^5$, Q, Z, Y, V, X and X' are as defined herein.

20 Claims, No Drawings

ARYLOXY- AND ARYLTHIOSUBSTITUTED PYRIMIDINES AND TRIAZINES AND DERIVATIVES THEREOF

This application claims the benefit of U.S. Provisional Application No. 60/014,213, filed Mar. 27, 1996.

FIELD OF THE INVENTION

The present invention relates to novel compounds, pharmaceutical compositions containing said compounds and to methods of using same in the treatment of affective disorders, anxiety, depression, post-traumatic stress disorders, eating disorders, supranuclear palsey, irritable bowl syndrome, immune supression, Alzheimer's disease, gastrointestinal diseases, anorexia nervosa, drug and alcohol withdrawal symptoms, drug addiction, inflammatory disorders, or fertility problems.

BACKGROUND OF THE INVENTION

Corticotropin releasing factor (herein referred to as CRF), a 41 amino acid peptide, is the primary physiological regulator of proopiomelanocortin(POMC)-derived peptide secretion from the anterior pituitary gland [J. Rivier et al., *Proc. Nat. Acad. Sci.* (USA) 80:4851 (1983); W. Vale et al., *Science* 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence demonstrating that CRF may also play a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data has demonstrated that CRF may have implications in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul, Peptides* 16:83 (1986)]. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

In order to study these specific cell-surface receptor proteins, compounds must be identified which can interact with the CRF receptor in a specific manner dictated by the pharmacological profile of the characterized receptor. Toward that end, there is evidence that the direct CRF antagonist compounds and compositions of this invention, that can attenuate the physiological responses to stress-related disorders, will have potential therapeutic utility for the treatment of depression and anxiety-related disorders. All of the aforementioned references are hereby incorporated by reference.

PCT Application US94/1105 teaches 1N-alkyl-N-arylpyrimidines and derivatives thereof in the treatment of affective disorders, anxiety, depression, post-traumatic stress disorders, eating disorders, supranuclear palsey, irritable bowl syndrome, immune supression, Alzheimer's disease, gastrointestinal diseases, anorexia nervosa, drug and alcohol withdrawal symptoms, drug addiction, inflammatory disorders, or fertility problems.

U.S. Pat. No. 5,062,882 teaches the synthesis of aryloxy- and arylthiotriazines useful as herbicides.

U.S. Pat. Nos. 4,427,437 and 4,460,588 describe the synthesis of aryloxy- and arylthiopyrimidines useful for the killing of internal parasites, especially trematodes and nematodes, in warm blooded animals, and/or as herbicides for inhibiting the growth of severely damaging or killing plants.

U.S. Pat. No. 5,281,707 teaches the synthesis and utility of water-soluble aryloxy triazines, useful for the thermal and photochemical stabilization of polyamide fiber materials.

The compounds and methods of the present invention provide the methodology for the production of specific high-affinity compounds capable of inhibiting the action of CRF at its receptor protein in the brain. These compounds would be useful in the treatment of a variety of neurodegenerative, neuropsychiatric and stress-related disorders. It is further asserted that this invention may provide compounds and pharmaceutical compositions suitable for use in such a method. Further advantages of this invention will be clear to one skilled in the art from the reading of the description that follows.

SUMMARY OF THE INVENTION

The present invention relates to novel 2-aryloxy- and 2-arylthiosubstituted pyrimidines and triazines and derivatives thereof, pharmaceutical compositions containing such compounds and method of using them in the treatment affective disorders, anxiety, depression, post-traumatic stress disorders, eating disorders, supranuclear palsey, irritable bowl syndrome, immune supression, Alzheimer's disease, gastrointestinal diseases, anorexia nervosa, drug and alcohol withdrawal symptoms, drug addiction, inflammatory disorders, or fertility problems. Said compounds interact with and have antagonist activity at the CRF receptor and thus have therapeutic effect.

[1] This invention provides compounds of formula (I):

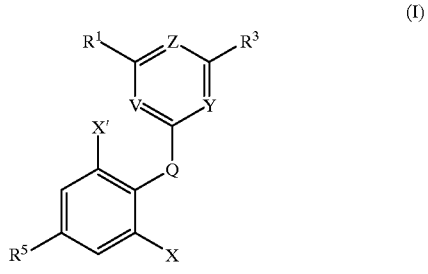

(I)

or a pharmaceutically acceptable salt or prodrug thereof, wherein:

Q=O, S(O)n;

$R^1$ is $C_1$–$C_4$-alkyl, -alkenyl, -alkynyl, $C_1$–$C_2$ haloalkyl, halogen, $NR^6R^7$, $OR^8$, $SR^8$, CN;

$R^3$ is $C_1$–$C_8$ alkyl, $C_1$–$C_2$ haloalkyl, halogen, $NR^6R^7$, $OR^8$, $SR^8$,$(CH_2)_kNR^6R^7$, $(CH_2)_kOR^8$, $CH(CHR^{16}CHR^{16}OR^8)_2$, $CH(CN)AR$, $CH(CN)_2$, $CHR^{16}(CHR^{16})_pOR^8$, $(CHR^{16})_pAr$ wherein the aryl group is substituted with 1–3 $R^{18}$, $(CHR^{16})_p$heteroaryl wherein the heteroaryl group is substituted with 1–3 $R^{18}$, 1-tetrahydroquinolinyl, 2-tetrahydroisoquinolinyl, phenyl or heteroaryl substituted with 0–3 groups chosen from hydrogen, halogen, $C_1$–$C_4$ alkyl, $C_1$–$C_4$ alkoxy, nitro, cyano, S(O)Z—$(C_1$–$C_6)$alkyl;

V is N;

Y is $CR^2$ or N;

Z is N;

$R^2$ and is independently selected at each occurrence from the group consisting of hydrogen, halo, halomethyl, methyl cyano, nitro, $NR^6R^7$, $NH(COR^9)$, $N(COR^9)$;

X and X' are independently selected at each occurrence from the group consisting of alkyl, halogen, $S(O)_nR^8$, $OR^8$, halomethyl, $NR^{14}R^{15}$, CN;

$R^5$ is H, halo, $C_1$–$C_6$ alkyl, $C_2$–$C_6$ alkenyl, $C_1$–$C_3$ haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_4$–$C_6$ cycloalkenyl, CN;

$R^6$ and $R^7$ are independently selected at each occurrence from the group consisting of: hydrogen, $C_1$–$C_6$ alkyl, $C_3$–$C_{10}$ cycloalkyl, $C_3$–$C_{10}$ cycloalkylalkyl, $CH(R^{16})(CHR^{16})_pOR^8$, $(CHR^{16})_pOR^8$, —$(C_1$–$C_6$ alkyl)-aryl, heteroaryl, —$(C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, amino, $NHC(=O)(C_1$–$C_6$ alkyl), $NH(C_1$–$C_6$ alkyl) $N(C_1$–$C_6$ alkyl$)_2$, nitro, $CO_2(C_1$–$C_6$ alkyl), cyano, $S(O)_z$—$(C_1$–$C_6$-alkyl), or $R^6$ and $R^7$ can be taken together to form —$(CH_2)_qA(CH_2)_r$—, optionally substituted with 0–3 $R^{17}$, or, when considered with the commonly attached nitrogen, $R^6$ and $R^7$ can be taken together to form a heterocycle, said heterocycle being substituted on carbon with 1–3 groups consisting of: hydrogen, $C_1$–$C_6$ alkyl, $(C_1$–$C_6)$alkyl$(C_1$–$C_4)$alkoxy, hydroxy, or $C_1$–$C_6$ alkoxy;

A is $CH_2$, O, $S(O)_n$, $N(C(=O)R^{24})$, $N(R^{19})$, $C(H)(NR^{14}R^{15})$, $C(H)(OR^{20})$, $C(H)(C(=O)R^{21})$, $N(S(O)_nR^{21})$;

$R^8$ is hydrogen, $C_1$–$C_6$ alkyl, $C_3$–$C_6$ cycloalkyl, $(CH_2)_tR^{22}$, $C_3$–$C_{10}$ cycloalkyl, cycloalkylalkyl, —$(C_1$–$C_6$ alkyl)-aryl, heteroaryl, —$(C_1$–$C_6$ alkyl)-heteroaryl or aryl optionally substituted with 1–3 groups selected from the following: hydrogen, halogen, $C_1$–$C_6$ alkyl $C_1$–$C_6$ alkoxy, amino, $NHC(=O)(C_1$–$C_6$ alkyl), $NH(C_1$–$C_6$ alkyl) $N(C_1$–$C_6$ alkyl$)_2$, nitro, $CO_2(C_1$–$C_6$ alkyl), cyano; $S(O)_z(C_1$–$C_6$-alkyl);

$R^9$ is independently selected at each occurrence from hydrogen, $C_1$–$C_4$ alkyl, $C_1$–$C_4$ alkoxy, $C_3$–$C_6$ cycloalkyl, $C_2$–$C_4$ alkenyl, aryl substituted with 0–3 $R^{18}$, and —$(C_1$–$C_6$ alkyl)-aryl substituted with 0—3 $R^{18}$;

$R^{14}$ and $R^{15}$ are independently hydrogen, $C_1$–$C_6$ alkyl, $C_3$–$C_6$ cycloalkyl, $(CH_2)_tR^{22}$, aryl substituted with 0–3 $R^{18}$;

$R^{16}$ is hydrogen or $C_1$–$C_4$ alkyl;

$R^{17}$ is hydrogen, $C_1$–$C_4$ alkyl, $C_1$–$C_4$ alkoxy, halo, $OR^{23}$, $SR^{23}$, $NR^{23}R^{24}$, $(C_1$–$C_6)$ alkyl, $(C_1$–$C_4)$ alkoxy;

$R^{18}$ is hydrogen, $C_1$–$C_4$ alkyl, $C_1$–$C_2$ haloalkyl, $C_1$–$C_4$ alkoxy, $C(=O)R^{24}$, $NO_2$, halogen or cyano;

$R^{19}$ is $C_1$–$C_6$ alkyl, $C_3$–$C_6$ cycloalkyl, $(CH_2)_wR^{22}$, aryl substituted with 0–3 $R^{18}$;

$R^{20}$ is hydrogen, $C(=O)R^{22}$, $C_1$–$C_4$ alkyl, $C_2$–$C_4$ alkenyl;

$R^{21}$ is hydrogen, $C_1$–$C_4$ alkoxy, $NR^{23}R^{24}$, hydroxyl or $C_1$–$C_4$ alkyl;

$R^{22}$ is cyano, $OR^{24}$, $SR^{24}$, $NR^{23}R^{24}$, $C_3$–$C_6$ cycloalkyl;

$R^{23}$ and $R^{24}$ are independently selected at each occurrence from hydrogen or $C_1$–$C_4$ alkyl;

k is 1–4;

n is independently selected at each occurrence from 0–2;

p is 0–3;

q is 0–3;

r is 1–4;

t is independently selected at each occurrence from 1–6;

z=0–3;

w=1–6;

provided, however, that when Y is $CR^2$, then $R^3$ is $(CHR^{16})_p Ar$ wherein the aryl group is substituted with 1–3 $R^{18}$ or $(CHR^{16})_p$heteroaryl wherein the heteroaryl group is substituted with 1–3 $R^{18}$.

[2] Preferred are those compounds of claim 1 wherein:

$R^3$ is $C_1$–$C_4$ alkyl, $C_1$–$C_2$ haloalkyl, $NR^6R^7$, $OR^8$, $CH(CHR^{16}CHR^{16}OR^8)_2$, $CH(CN)AR$, $CH(CN)_2$, $CH(R^{16}CHR^{16})_p OR^8$, $(CHR^{16})_p Ar$ wherein the aryl group is substituted with 1–3 $R^{18}$, $(CHR^{16})_p$heteroaryl wherein the heteroaryl group is substituted with 1–3 $R^{18}$, 1-tetrahydroquinolinyl, 2-tetrahydroisoquinolinyl, phenyl or heteroaryl substituted with 0–3 groups chosen from hydrogen, halogen, $C_1$–$C_4$ alkyl, $C_1$–$C_4$ alkoxy, nitro, cyano, S(O)z—($C_1$–$C_6$) alkyl;

$R^2$ is independently selected at each occurrence from the group consisting of hydrogen, halo, methyl, nitro, cyano, NR6R7, NH(COR9), N(COR9)2;

$R^6$ and $R^7$ are independently selected at each occurrence from the group consisting of: hydrogen, $C_1$–$C_6$ alkyl, $C_3$–$C_{10}$ cycloalkyl, cycloalkylalkyl, $C_1$–$C_6$ alkoxy, $(CHR^{16})_p OR^8$, $(CHR^{16})_p OR^8$, —($C_1$–$C_6$ alkyl)-aryl, heteroaryl, —($C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, NHC(=O)($C_1$–$C_6$ alkyl), NH($C_1$–$C_6$ alkyl) N($C_1$–$C_6$ alkyl)$_2$, $CO_2$($C_1$–$C_6$ alkyl), cyano, or $R^6$ and $R^7$ can be taken together to form —$(CH_2)_q A(CH_2)_r$—, optionally substituted with 0–3 $R^{17}$, or, when considered with the commonly attached nitrogen, $R^6$ and $R^7$ can be taken together to form a heterocycle, said heterocycle being substituted on carbon with 1–3 groups consisting of: hydrogen, $C_1$–$C_6$ alkyl, ($C_1$–$C_6$) alkyl($C_1$–$C_4$)alkoxy, hydroxy, or $C_1$–$C_6$ alkoxy;

$R^8$ is hydrogen, $C_1$–$C_6$ alkyl, $C_3$–$C_6$ cycloalkyl, $(CH_2)_r R^{22}$, $C_3$–$C_{10}$ cycloalkyl, cycloalkylalkyl, —($C_1$–$C_6$ alkyl)-aryl, or hetero-aryl optionally substituted with 1–3 groups selected from the following: hydrogen, halogen, $C_1$–$C_6$ alkyl $C_1$–$C_6$ alkoxy, NHC(=O) ($C_1$–$C_6$ alkyl), NH($C_1$–$C_6$ alkyl) N($C_1$–$C_6$ alkyl)$_2$, $CO_2$($C_1$–$C_6$ alkyl);

$R^{14}$ and $R^{15}$ are independently hydrogen, $C_1$–$C_6$ alkyl, $C_3$–$C_6$ cycloalkyl;

$R^{17}$ is hydrogen, $C_1$–$C_4$ alkyl, $C_1$–$C_4$ alkoxy, ($C_1$–$C_6$) alkyl($C_1$–$C_4$)alkoxy;

$R^{18}$ is hydrogen, $C_1$–$C_4$ alkyl, $C_1$–$C_2$ haloalkyl, $C_1$–$C_4$ alkoxy, or cyano;

$R^{19}$ is $C_1$–$C_6$ alkyl, $C_3$–$C_6$ cycloalkyl, aryl substituted with 0–3 $R^{18}$;

$R^{22}$ is cyano, $OR^{24}$, $SR^{24}$, $NR^{23}R^{24}$, $C_3$–$C_6$ alkyl or cycloalkyl;

$R^{23}$ and $R^{24}$ are independently selected at each occurrence from hydrogen or $C_1$–$C_4$ alkyl;

t is independently selected at each occurrence from 1–3;

w is 1–3;

provided, however, that when Y is $CR^2$, then $R^3$ is $(CHR^{16})_p Ar$ wherein the aryl group is substituted with 1–3 $R^{18}$ or $(CHR^{16})$pheteroaryl wherein the heteroaryl group is substituted with 1–3 $R^{18}$.

[3] More preferred are those compounds of claim 2 wherein:

$R^1$ is $C_1$–$C_2$ alkyl, halide, $NR^6R^7$, $OR^8$;

$R^3$ is $C_1$–$C_4$ alkyl, $C_1$–$C_2$ haloalkyl, $NR^6R^7$, $OR^8$, $(CH_2)_k NR^6R^7$, $(CH_2)_k OR^8$;

Y is N;

X and X' are independently selected at each occurrence from the group consisting of methyl, hydrogen, Cl, Br, I, $OR^8$, $NR^{14}R^{15}$, CN, $S(O)n R^8$;

$R^5$ is H, halo, $C_1$–$C_6$ alkyl, $C_1$–$C_3$ haloalkyl, $C_1$–$C_6$ alkoxy, $(CHR^{16})_p OR^8$, $(CHR^{16})_p NR^{14}R^{15}$, $C_4$–$C_6$ cycloalkyl;

$R^6$ and $R^7$ are independently selected at each occurrence from the group consisting of: $C_1$–$C_6$ alkyl, $(CHR^{16})_p R^8$; or can be taken together to form —$(CH_2)_q A(CH_2)_r$—, optionally substituted with $CH_2OCH_3$;

A is $CH_2$, O, $S(O)_n$, N(C(=O)$R^{18}$), N($R^{19}$), C(H)(O$R^{20}$);

$R^8$ is hydrogen, $C_1$–$C_6$ alkyl, $C_3$–$C_6$ cycloalkyl, $(CH_2)_r R^{22}$;

$R^9$ is hydroxy, $C_1$–$C_4$ alkyl, or methoxy;

$R^{13}$ is $OR^{19}$, $SR^{19}$, $NR^{23}R^{24}$, $C_3$–$C_6$ cycloalkyl;

$R^{14}$ and $R^{15}$ are independently is hydrogen, $C_1$–$C_2$ alkyl, $C_3$–$C_6$ cycloalkyl;

$R^{16}$ is hydrogen;

$R^{18}$ is hydrogen, $C_1$–$C_4$ alkyl, $C_1$–$C_2$ haloalkyl, $C_1$–$C_4$ alkoxy, C(=O)$R^{24}$, or cyano; $R^{19}$ is $C_1$–$C_3$ alkyl;

$R^{20}$ is hydrogen, $C_1$–$C_2$ alkyl or $C_2$–$C_3$ alkenyl;

$R^{22}$ is $OR^{24}$;

$R^{23}$ and $R^{24}$ are independently selected at each occurrence from hydrogen or $C_1$–$C_2$ alkyl;

k is 1–3;

m is 1–4;

n is independently selected at each occurrence from 0–2;

p is 0–2;

q is 0–2;

r is 1–2;

t is independently selected at each occurrence from 1–3;

w is 1–3.

[4] Most preferred are those compounds of claim 1 selected from the group:

a) 2-[2-Bromo-6-methoxy-4(1-methylethenyl)phenoxy]-4-methyl-6-(4-morpholinyl)-1,3,5triazine;

b) 2-[2-Bromo-6-methoxy-4(1-methylethenyl)phenoxy]-4-methyl-6-(bis(2-methoxyethyl)amino)-1,3,5-triazine;

c) 2-[2-Bromo-6-methoxy-4(1-methylethenyl)phenoxy]-4-methyl-6-(N-propyl-N-cyclopropylmethylamino-1,3,5-triazine;

d) 2-[2-Bromo-6-methoxy-4(1-methylethenyl)phenoxy]-4-methyl-6-(1-homopiperidinyl)-1,3,5-triazine;

e) 2-[2-Bromo-6-methoxy-4(1-methylethenyl)phenoxy]-4-methyl-6-(diethylamino)-1,3,5-triazine;

f) 2-[2-Bromo-6-methoxy-4(1-methylethenyl)phenoxy]-4-methyl-6-(N-butyl-N-ethylamino)-1,3,5-triazine;

g) 2-[2-Bromo-6-methoxy-4(1-methylethenyl)phenoxy]-4-methyl-6-(4-thiomorpholinyl)-1,3,5-triazine;

h) 2-[2-Bromo-6-methoxy-4(1-methylethenyl)phenoxy]-4-methyl-6-(2-(1-methoxybutyl)amino)-1,3,5-triazine;

i) 2-[2-Bromo-6-methoxy-4(1-methylethenyl)phenoxy]-4-methyl-6-(1-piperidinyl)-1,3,5-triazine;

j) 2-[2-Bromo-6-methoxy-4(1-methylethenyl)phenoxy]-4-methyl-6-(1-(1.2.3.4-tetrahydroquinolinyl))-1,3,5-triazine;

k) 2-[2-Bromo-6-methoxy-4(1-methylethenyl)phenoxy]-4-methyl-6-(1-pyrrolidinyl)-1,3,5-triazine;

l) 2-[2-Bromo-6-methoxy-4(1-methylethenyl)phenoxy]-4-methyl-6-(1-(2-ethylpieridinyl))-1,3,5-triazine;

m) 2-[2-Bromo-6-methoxy-4(1-methylethenyl)phenoxy]-4-methyl-6-(2-(1.2.3.4-tetrahydroisoquinolinyl))-1,3,5-triazine;

n) 2-[2-Bromo-6-methoxy-4(1-methylethenyl)phenoxy]-4-methyl-6-(1-(1,3,5,6-tetrahyropiperidinyl)-1,3,5-triazine;
o) 2-[2-Bromo-6-methoxy-4(1-methylethenyl)phenoxy]-4-methyl-6-(1-(2-trifluoromethylphenyl))-1,3,5-triazine;
p) 2-[2-Bromo-6-methoxy-4(1-methylethyl)phenoxy]-4-methyl-6-(4-morpholinyl)-1,3,5-triazine;
q) 2-[2-Bromo-6-methoxy-4(1-methylethyl)phenoxy]-4-methyl-6-(bis(2-methoxyethyl)amino)-1,3,5-triazine;
r) 2-[2-Bromo-6-methoxy-4(1-methylethyl)phenoxy]-4-methyl-6-(N-propyl-N-cyclopropylmethylamino)-1,3,5-triazine;
s) 2-[2-Bromo-6-methoxy-4(1-methylethyl)phenoxy]-4-methyl-6-(1-homopiperidinyl)-1,3,5-triazine;
t) 2-[2-Bromo-6-methoxy-4(1-methylethyl)phenoxy]-4-methyl-6-(N-butyl-N-ethylamino)-1,3,5-triazine;
u) 2-[2-Bromo-6-methoxy-4(1-methylethyl)phenoxy]-4-methyl-6-(4-thiomorpholinyl)-1,3,5-triazine;
v) 1-[3-Bromo-5-methoxy-4-[[4-methyl-6-(4-morpholinyl)-1,3,5-triazinyl-2-yl]oxy]phenyl]ethanone;
w) 1-[3-Bromo-5-methoxy-4-[[4-methyl-6-(bis(2-methoxyethyl)amino)-1,3,5-triazinyl-2-yl]oxy]phenyl]ethanone;
x) 1-[3-Bromo-5-methoxy-4-[[4-methyl-6-(4-thiomorpholinyl)-1,3,5-triazinyl-2-yl]oxy]phenyl]ethanone;
y) 1-[3-Bromo-5-methoxy-4-[[4-methyl-6-(diethylamino)-1,3,5-triazinyl-2-yl]oxy]phenyl]ethanone;
z) 1-[3-Bromo-5-methoxy-4-[[4-methyl-6-(1-piperidinyl)-1,3,5-triazinyl-2-yl]oxy]phenyl]ethanone;
aa) 3-Bromo-4-[[6-methyl-4(bis(2-methoxyethyl)amino)-1,3,5-triazin-2-yl]oxy]-5-methoxy-alpha,alpha-dimethylbenzenemethanol;
bb) 3-Bromo-4-[[6-methyl-4(N-propyl-N-cyclopropylmethylamino)-1,3,5-triazin-2-yl]oxy]-5-methoxy-alpha,alpha-dimethylbenzenemethanol;
cc) 3-Bromo-4-[[6-methyl-4(2-(1-methoxybutyl)amino)-1,3,5-triazin-2-yl]oxy]-5-methoxy-alpha,alpha-dimethylbenzenemethanol;
dd) 3-Bromo-4-[[6-methyl-4(4-thiomormopholinyl)-1,3,5-triazin-2-yl]oxy]-5-methoxy-alpha,alpha-dimethylbenzenemethanol;
ee) 3-Bromo-4-[[6-methyl-4(1-piperidinyl)-1,3,5-triazin-2-yl]oxy]-5-methoxy-alpha,alpha-dimethylbenzenemethanol;
ff) 3-Bromo-4-[[6-methyl-4(1-homopiperidinyl)-1,3,5-triazin-2-yl]oxy]-5-methoxy-alpha,alpha-dimethylbenzenemethanol;
gg) 3-Bromo-4-[[6-methyl-4(1-(2-trifluoromethylphenyl))-1,3,5-triazin-2-yl]oxy]-5-methoxy-alpha,alpha-dimethylbenzenemethanol;
hh) 2-(2,4,6-Triodophenoxy)-4-methyl-6-(4-morpholinyl)-1,3,5-triazine;
ii) 2-(2,4,6-Trichlorophenoxy)-4-methyl-6-(4-morpholinyl)-1,3,5-triazine;
jj) 2-(2-chloro-4,6-Dimethoxyphenoxy)-4-methyl-6-(4-morpholinyl)-1,3,5-triazine; and
kk) 2-[(2,6-Dibromo-4-(1-methylethyl))phenoxy]-4-methyl-6-(N-ethyl-N-butylamino)-1,3,5-triazine uu) 2-[(2,6-Dibromo-4-(1-methylethyl))phenoxy]-4-methyl-6-(bis(2-methoxyethyl)amino)-1,3,5-triazine.

[5] Also provided by this invention is method of treating affective disorders, anxiety, or depression in mammals comprising administering to the mammal a therapeutically effective amount of a compound provided herein.

[6] Also provided by this invention are pharmaceutical compositions comprising a pharmaceutically acceptable carrier and a therapeutically effective amount of a compound provided herein.

[7] The compounds provided by this invention (and especially labelled compounds of this invention) are also useful as standards and reagents in determining the ability of a pharmaceutical drug or other chemical compound to bind to the CRF receptor. These would be provided in commercial kits comprising a compound provided by this invention.

DETAILED DESCRIPTION OF INVENTION

In the present invention it has been discovered that the provided compounds are useful as antagonists of Corticotropin Releasing Factor and for the treatment of affective disorders, anxiety, or depression.

The present invention also provides methods for the treatment affective disorder, anxiety or depression by administering to a compromised host a pharmaceutically or therapeutically effective or acceptable amount of a compound of formula (I) as described above. By therapeutically effective amount, it is meant an amount of a compound of the present invention effective to antagonize abnormal level of CRF or treat the symptoms of affective disorder, anxiety or depression in a host.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$ through $R^{10}$, m, n, A, W, Z, etc.) occurs more than one time in any constituent or in formula (I), or any other formula herein, its definition on each occurrence is independent of its definition at every other occurrence. Thus, for example, in —$NR^8R^9$, each of the substituents may be independently selected from the list of possible $R^8$ and $R^9$ groups defined. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more triple carbon-carbon bonds which may occur in any stable point along the chain, such as ethynyl, propynyl and the like. "Haloalkyl" is intended to include both branched and straight-chain saturated aliphatic hydrocarbon groups having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" as used herein refers to fluoro, chloro, bromo, and iodo.

As used herein, "aryl" or "aromatic residue" is intended to mean phenyl, biphenyl or naphthyl. The term "heteroaryl" is meant to include unsubstituted, monosubstituted or disubstituted 5-, 6- or 10-membered mono- or bicyclic aromatic rings which can optionally contain from 1 to 3 heteroatoms selected from the group consisting of O, N, and S and are expected to be active. Included in the definition of the group heteroaryl, but not limited to, are the following: 2-, or 3-, or 4-pyridyl; 2- or 3-furyl; 2- or 3-benzofuranyl; 2-, or 3-thiophenyl; 2- or 3-benzo[b]thiophenyl; 2-, or 3-, or 4-quinolinyl; 1-, or 3-, or 4-isoquinolinyl; 2- or 3-pyrrolyl; 1- or 2- or 3- indolyl; 2-, or 4-, or 5-oxazolyl; 2-benzoxazolyl 2- or 4- or 5-imidazolyl; 1- or 2-benzimidazolyl; 2- or 4- or 5-thiazolyl; 2-benzothiazolyl; 3- or 4- or 5-isoxazolyl; 3- or 4- or 5-pyrazolyl; 3- or 4- or 5-isothiazolyl; 3- or 4-pyridazinyl; 2- or 4- or 5-pyrimidinyl; 2-pyrazinyl; 2-triazinyl; 3- or 4-cinnolinyl; 1-phthalazinyl; 2- or 4-quinazolinyl; or 2-quinoxalinyl ring. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

The novel substituted-2-pyrimidinamines and substituted triazines of the present invention may be prepared by one of the general schemes outlined below where $R^1$, $R^3$, $R^5$, Q, X, X', etc. are as defined above.

Compounds of the Formula (I), wherein V, Y and Z are N, can be prepared as shown in Schemes 1 and 2. For instance, treatment of acetovanillone (II, X=0 Me) with bromine in a halogenated solvent, such as, but not limited to, 1,2-dichloroethane or chloroform provides 3-bromo-4-hydroxy-5-methoxyacetophenone (III) which upon condensation with a Grignard reagent such as methyl magnesium bromide in an aprotic solvent such as, but not limited to, diethyl ether or THF, gives the tertiary carbinol (IV, $R^{16}$=H). Deprotonation of IV with sodium hydroxide in a solvent such as water or alcohol followed by treatment of the resulting phenoxide with 4,6-dichloro-2-methyltriazine (V) in solvents such as acetonitrile or DMF affords the chlorophenoxytriazine (VI). *Helv. Chim. Acta.*, 33, 1365 (1950). Treatment of the triazine VI with various primary or secondary amines such as morpholine in solvents such as, but not limited to, dioxane, ethylene glycol, methoxyethoxyethanol, etc., produces the aminophenoxytriazine (VII). Acid catalyzed dehydration of carbinol (VII) in solvents such as benzene, toluene, THF, etc., yields the olefin (VIII) which upon hydrogenation in the presence of a catalyst such as platinum black furnishes the 4-alkyl substituted phenoxy derivatives (IX).

Utilization of other Grignard reagents provides the opportunity of producing compounds with different alkyl groups at the 4-position of the phenyl ring in Formula IV, VI, VII, VIII and IX of Scheme 1. The variations at the 4-position of the triazine ring are also considerable and include not only secondary (from primary amines) and tertiary (from secondary amines) amino groups $R^6$ and $R^7$ in Scheme 1, but also aryl and heteroaryl substituents derived from the appropriate organometallic reagents as shown in Schemes 3 and 4.

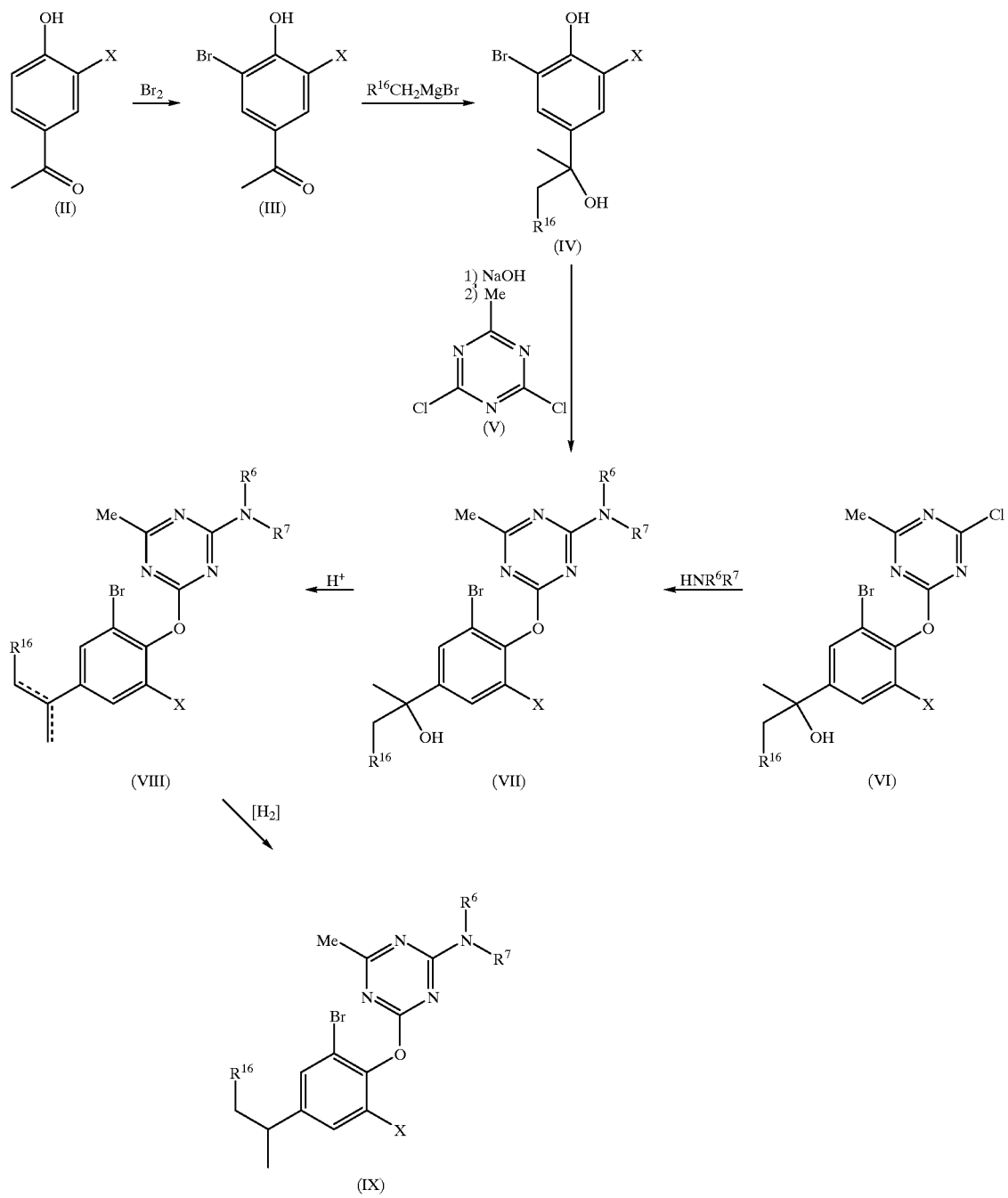

Scheme 1

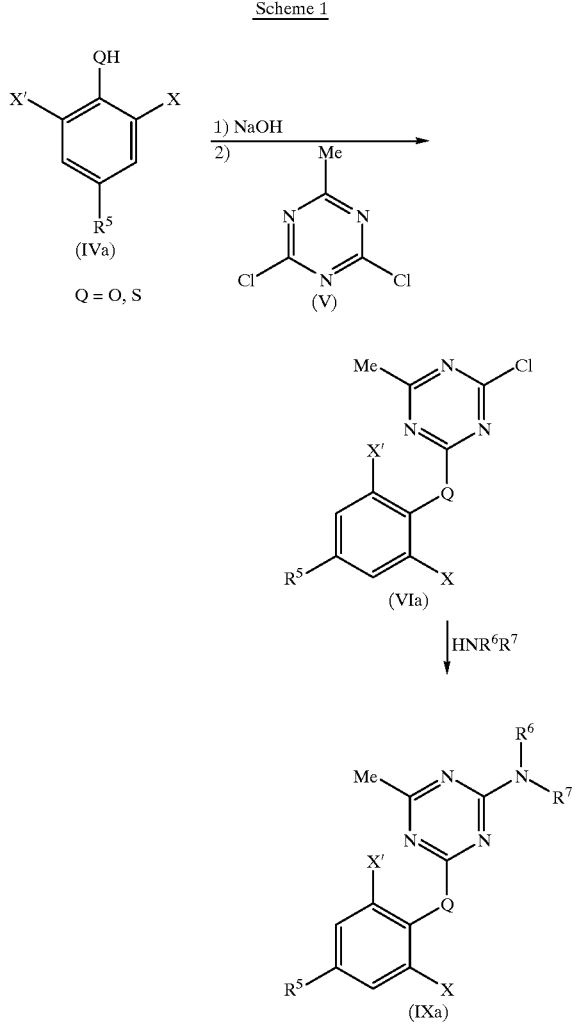

Scheme 2

The compounds of Formula (I), wherein X and X' are halogen or methyl, can also be prepared as shown in Scheme 2 by utilizing the appropriately 4-substituted 2,6-dihalo- or 2,6-dimethyl-phenols (IVa). These compounds are prepared from a variety of substituted phenols which are commercially available such as, but not limited to, the 2,4,6-trichloro-, 2,4,6-tribromo- and 2,4,6-trimethyl-phenols, or are obtained by established literature methods by one skilled in the art. Subsequent to condensation with V to provide the aryloxychloropyrimidine (VIa), amination can provide target compounds IXa which represent Formula I where X and X' are defined above, with $R^1$, $R^3$ and $R^5$ are as previously described, and Q is O.

Alternatively, the phenols of Schemes 1 and 2 may be replaced with the appropriately sustituted thiophenols, to prepare the corresponding sulfur analogs of those compounds described in these schemes (Q=S). These, in turn, may be oxidized to the the corresponding sulfoxides or sulfones by oxidizing agents such as, but not limited to, oxone, sodium metaperiodate, potassium permanganate, m-chloroperbenzoic acid, dimethyl dioxirane, peracetic acid, hydrogen peroxide, etc.

Compounds of Formula I where Y is $CR^2$ and $R^3$ is selected from $(CHR^{16})_p Ar$ wherein the aryl group is substituted with 1–3 $R^{18}$, $(CHR^{16})_p$heteroaryl wherein the heteroaryl group is substituted with 1–3 $R^{18}$, can be prepared as shown in Scheme 3. Treatment of IVa with a base such as sodium hydroxide in a protic solvent such as water or alcohol, followed by condensation of the resulting phenoxide with the known 4,6-dichloro-2-methyl-5-nitro-pyrimidine [*J. Chem. Soc.* 3832 (1954); ibid, 677 (1944)] yields the aryloxychloronitropyrimidine, Xa. Reaction of Xa with an organometallic reagent, $R^3M$, wherein M is magnesium or magnesium halide or lithium or another appropriate metal, with or without catalysts such as copper, nickel, palladium or zinc, provides aryloxy-, aryl- or heteroarylnitropyrimidine, XIa. *Comprehensive Organic Chemistry*, vol 13, Chapter 15, (Barton and Ollis, eds.; Pergamon, N.Y.). XIa can then be reduced with iron powder in acetic acid to give the amino pyrimidine derivative (XIIIa). This amino group can be further transformed into various substituted aryloxypyrimidines (XVa) utilizing standard amino group transformation technology. This methodology includes, but is not limited to, diazonium salt chemistry (Sandmeyer, etc.), acylation chemistry, reductive amination chemistry, etc. The sequence described in Scheme 4 gives further example of this process.

Treatment of the carbinol (IV) with sodium hydroxide in a protic solvent such as water or alcohol, followed by condensation of the resulting phenoxide with the known 4,6-dichloro-2-methyl-5-nitro-pyrimidine [*J. Chem. Soc.* 3832 (1954); ibid, 677 (1944)] yields the aryloxychloronitropyrimidine (X). Reaction of X with an organometallic reagent, $R^3M$, wherein M is magnesium or magnesium halide or lithium or another appropriate metal, with or without catalysts such as copper, nickel, palladium or zinc, provides aryloxy-, aryl- or heteroarylnitropyrimidine, XI. *Comprehensive Organic Chemistry*, vol 13, Chapter 15, (Barton and Ollis, eds.; Pergamon, N.Y.). XI can be dehydrated to the olefin XII with acid catalysis. Reduction of the nitro group may be achieved using Fe powder in acetic acid to provide the diaminopyrimidine (XIII) that could be acetylated with acetyl chloride in the presence of a tertiary amine, such as triethylamine, in a solvent, such as dichloromethane, to the acetamide (XIV). Alternatively, XII could be successively hydrogenated over platinum black on charcoal to provide nitropyrimidine (XV) and aminopyrimidine (XVI), respectively.

Alternatively, the phenols of Schemes 3 and 4 may be replaced with the appropriately sustituted thiophenols, to prepare the corresponding sulfur analogs of those compounds described in these schemes (Q=S). These, in turn, i.e., XIV, XV, XVa, may be oxidized to the the corresponding sulfoxides or sulfones by oxidizing agents such as, but not limited to, oxone, sodium metaperiodate, potassium permanganate, m-chloroperbenzoic acid, dimethyl dioxirane, peracetic acid, hydrogen peroxide, etc SCHEME 3
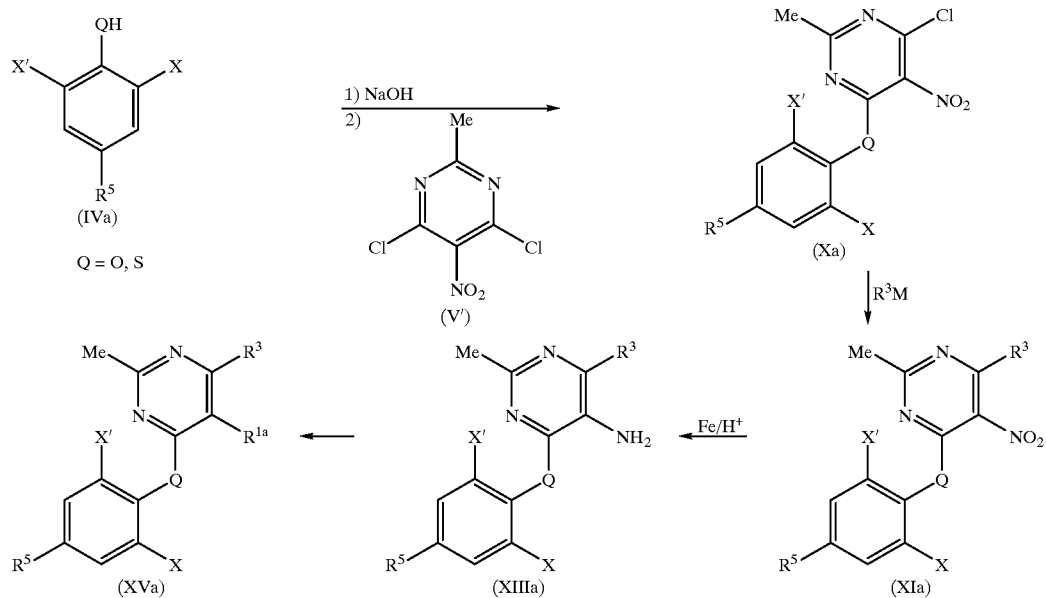
SCHEME 4
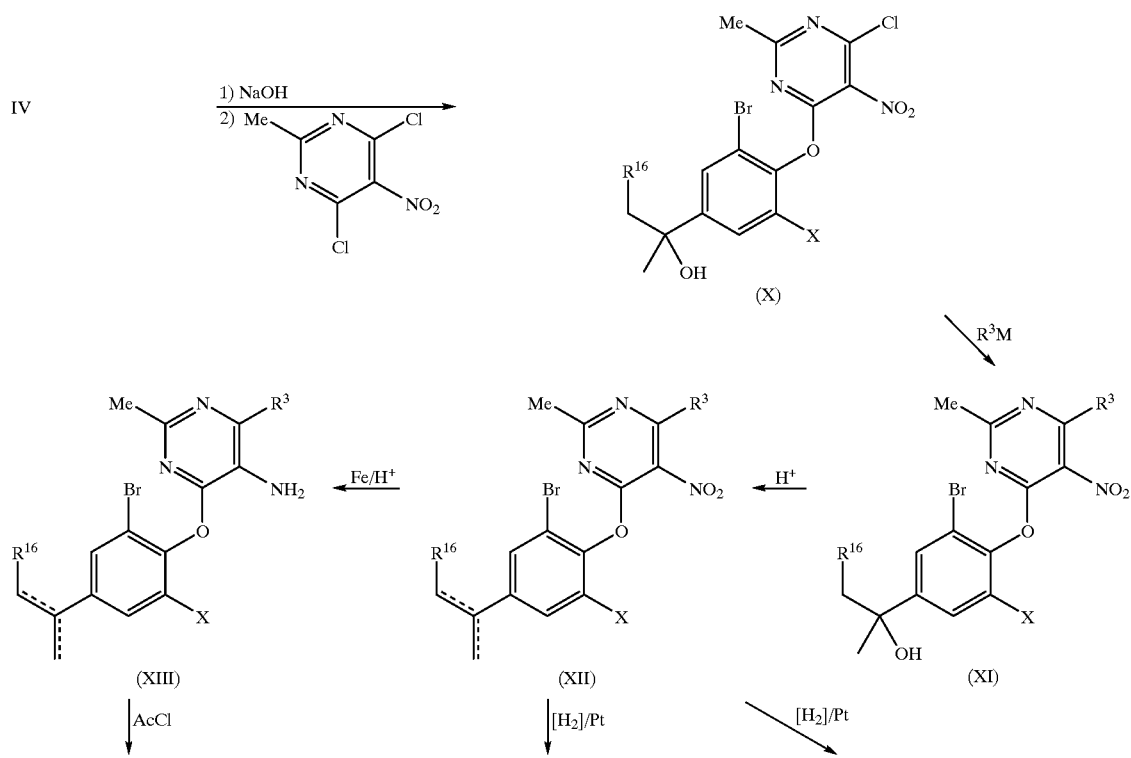

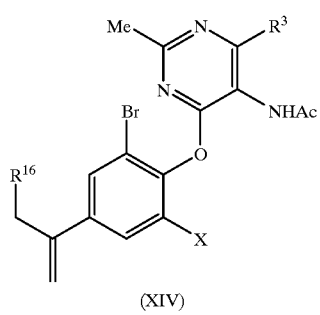 (XIV)

-continued

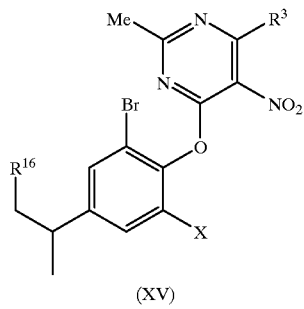 (XV)

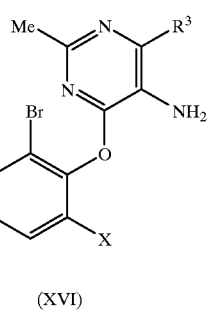 (XVI)

The compounds of the intervention and their synthesis are further illustrated by the following examples and preparations.

EXAMPLE 1

3-Bromo-4-hydroxy-5-methoxyacetophenone

Bromine (9.62 g) in 30 mL of chloroform was added dropwise to a solution of acetovanillone (10.0 g) in 150 mL of chloroform maintained at 0°–5° C., such that the temperature did not rise above 5° C. After the addition was complete, the mixture was stirred at 0°–5° C. for 4 hours. The residue was treated with water. The organic layer was dried over $MgSO_4$ and stripped of the solvent under reduced pressure to yield a pinkish powder which was tritrated with ether and filtered to yield 3-bromo-4-hydroxy-5-methoxyacetophenone, mp 148–152° C.

EXAMPLE 2

3-Bromo-4-hydroxy-5-methoxy-a,a-dimethylbenzenemethanol

Methyl magnesium bromide (3 M in diethyl ether, 11.42 mL) was added dropwise to a solution of 5-Bromo-4-hydroxy-3-methoxyacetophenone (3.0 g) in anhydrous tetrahydrofuran (60 mL) maintained at 0°–5° C. under $N_2$ gas, such that the temperature did not rise above 50° C. After the addition was complete, the solution was stirred at room temperature for 2 hours. Saturated ammonium chloride was added dropwise until effervescence ceased. The mixture was treated with an excess of saturated ammonium chloride. The organic layer was dried over $MgSO_4$ and stripped of the solvent under reduced pressure to yield 3-bromo-4-hydroxy-5-ethoxy-a,a-dimethylbenzenemethanol as a viscous oil which solidified over a period of time, mp 107–112° C.

EXAMPLE 3

3-Bromo-4-[[4-chloro-6-methyl-1,3,5-triazin-2-yl]oxy]-5-methoxy-a,a-dimethylbenzenemethanol 3-bromo-4-hydroxy-5-methoxy-a,a-dimethylbenzenemethanol (1.16 g) was dissolved in 10% NaOH (1.78 g) and 5 mL of water. The solvent was stripped under reduced pressure. The salt was taken up in 50 mL acetonitrile and cooled to 0°–5° C. 2,4-dichloro-6-methyl-1,3,5-triazine (0.61g) was added and the mixture was stirred at 0°–5° C. for 1 hour. The solvent was removed under reduced pressure and the residue was extracted with methylene chloride. The extracts were combined and stripped under reduced pressure to yield 3-bromo-4-[[4-chloro-6-methyl-1,3,5-triazin-2-yl]oxy]-5-methoxy-a,a-dimethylbenzenemethanol.

EXAMPLE 4

3-Bromo-4-[[6-methyl-4-(4-morpholinyl)-1,3 5-triazin-2-yl]oxy]-5-methoxy-a,a-dimethylbenzenemethanol To a solution of 3-bromo-4-[[4-chloro-6-methyl-1,3,5-triazin-2-yl]oxy]-5-methoxy-a,a-dimethylbenzenemethanol (3.0 g) in anhydrous 1,4-dioxane (80 mL), morpholine (1.39 mL) was added and the solution was stirred at room temperature for 2 hours. The solvent was removed under reduced pressure and the residue was taken up in water and extracted with methylene chloride. The extracts were combined and dried over $MgSO_4$. The solvent was stripped under reduced pressure and the residue was purified on silica gel using a 2:1 mixture of ethyl acetate and hexane to yield 3-bromo-4-[[6-methyl-4-(4-morpholinyl)-1,3,5-triazin-2-yl]oxy]-5-methoxy-a,a-dimethylbenzenemethanol as a colorless powder, mp 199–201° C.

TABLE 1

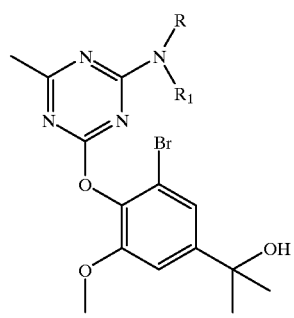

| R | $R_1$ | MP (° C.) |
|---|---|---|
| $CH_2CH_2OCH_3$ | $CH_2CH_2OCH_3$ | 92–94 |
| $CH_2CH_2CH_3$ | $CH_2(CHCH_2CH_2)$ | 144–147 |
| H | $CH(CH_2CH_3)CH_2OCH3$ | |
| | $(CH_2)_5$ | 86–98 |
| | $(CH_2)_4$ | 152–153 |
| | $CH_2CH_2SCH_2CH_2$ | 161–167 |

EXAMPLE 5

2-[2-bromo-6-methoxy-4-(1-methylethenyl)phenoxy]-4-methyl-6-(4-morpholinyl)-1,3,5-triazine To a solution of 3-bromo-4-[[6-methyl-4-(4-morpholinyl)-1,3,5-triazin-2-yl]oxy]-5-methoxy-a,a-dimethylbenzenemethanol (1.92 g) in 80 mL of benzene, a small amount of p-toluene sulfonic acid was added. The solution was refluxed under azeotropic conditions for 16 hours. Once cooled to room temperature, the solution was washed with saturated NaHCO$_3$ followed by water. The organic phase was dried over MgSO$_4$ and the solvent was removed under reduced pressure. The residue was purified on silica gel using a mixture of 1:1 ethyl acetate and hexane to yield 2-[2-bromo-6-methoxy-4-(1-methylethenyl) phenoxy]-4-methyl-6-(4-morpholinyl)-1,3,5-triazine as a colorless compound, mp 63–67° C.

TABLE 2

| R | R$_1$ | MP (° C.) |
|---|---|---|
| | CH$_2$CH$_2$OCH$_2$CH$_2$ | 63–67 |
| CH$_2$CH$_2$OCH$_3$ | CH$_2$CH$_2$OCH$_3$ | |
| CH$_2$CH$_2$CH$_3$ | CH$_2$(CHCH$_2$CH$_2$) | oil |
| CH$_2$CH$_3$ | CH$_2$CH$_2$CH$_2$CH$_3$ | oil |
| H | CH(CH$_2$CH$_3$)CH$_2$OCH$_3$ | 119–121 |
| | CH$_2$CH$_2$SCH$_2$CH$_2$ | 147–151 |
| | (CH$_2$)$_5$ | |
| | (CH$_2$)$_4$ | 154–161 |
| | (CH$_2$)$_6$ | 103–105 |
| (CH$_2$)$_4$CH(CH$_2$CH$_3$) | | 58–64 |
| | CH$_2$CH$_2$CHCHCH$_2$ | 51–54 |
| tetrahydroisoquinoline | | |
| tetrahydroquinoline | | 63–79 |

EXAMPLE 6

2-[2-bromo-6-methoxy-4-(1-methylethenyl) phenoxy]-4-methyl-6-(4-morpholinyl)-1,3.5-triazine Platinum black, 5% (0.20 g) was added to a solution of 2-[2-bromo-6-methoxy-4-(1-methylethenyl)phenoxy]-4-methyl-6-(4-morpholinyl)-1,3,5-triazine (0.18 g) in 50 mL of ethanol. The mixture was hydrogenated at a pressure of 27 psi for 16 hours. The mixture was filtered through celite and the filtrate was stripped under reduced pressure to yield 2-[2-bromo-6-methoxy-4-(1-methylethenyl)phenoxy]-4-methyl-6-(4-morpholinyl)-1,3,5-triazine as a colorless powder, mp 131–133° C.

TABLE 3

| R | R$_1$ | MP (° C.) |
|---|---|---|
| CH$_2$CH$_2$OCH$_3$ | CH$_2$CH$_2$OCH$_3$ | |
| CH$_2$CH$_2$CH$_3$ | CH$_2$(CHCH$_2$CH$_2$) | |
| H | CH(CH$_2$CH$_3$)CH$_2$OCH$_3$ | 121–127 |
| | CH$_2$CH$_2$OCH$_2$CH$_2$ | 131–133 |
| | CH$_2$CH$_2$SCH$_2$CH$_2$ | 112–118 |

EXAMPLE 7

1-[3-bromo-5-methoxy-4-[[4-methyl-6-(4-morpholinyl)-1,3,5-triazin-2-yl]oxy]phenyl]ethanone 3-bromo-4-hydroxy-5-methoxyacetophenone (3.60 g) was dissolved in 10% NaOH (5.86 g) and 10 mL of water. The solvent was stripped under reduced pressure. The salt was taken up in 50 mL acetonitrile and cooled to 0°–5° C. 2,4-dichloro-6-methyl-1,3,5-triazine (2.40 g) was added and the mixture was stirred at 0°–5° C. for 1 hour. The solvent was then removed from the mixture under reduced pressure. The residue was extracted with methylene chloride. The extracts were combined and stripped under reduced pressure to yield a solid which was dissolved in 120 mL of anhydrous 1,4-dioxane and the resulting solution treated with 2.64 mL of morpholine. The mixture was stirred at room temperature for 2 hours and the solvent was then removed under reduced pressure. The residue was taken up in water and extracted with methylene chloride. The combined methylene chloride extracts were dried over MgSO$_4$ and evaporated under reduced pressure to yield 1-[3-bromo-5-methoxy-4-[[-methyl-6-(4-morpholinyl)-1,3,5-triazin-2-yl]oxy]phenyl] ethanone, mp 159–162° C.

TABLE 4

| R | R$_1$ | MP (° C.) |
|---|---|---|
| CH$_2$CH$_2$OCH$_3$ | CH$_2$CH$_2$OCH$_3$ | 82–86 |
| CH$_2$CH$_3$ | CH$_2$CH$_3$ | 125–127 |

TABLE 4-continued

[Structure: 1,3,5-triazine with methyl group, and -N(R)(R1) substituent, connected via O to a brominated, methoxy-substituted phenyl ring bearing an acetyl group]

| R | $R_1$ | MP (° C.) |
|---|---|---|
| CH$_2$CH$_2$OCH$_2$CH$_2$ | | 159–162 |
| CH$_2$CH$_2$SCH$_2$CH$_2$ | | 158–170 |
| (CH$_2$)$_5$ | | 111–115 |

Utility

In vitro Receptor Binding Assay

Tissue Preparation: Male Sprague Dawley rats (180–200 g) were sacrificed by decapitation and the cortex was dissected on ice, frozen whole in liquid nitrogen and stored at −70° C. until use. On the day of assay, frozen tissue was weighed and homogenized in 20 volumes of ice cold buffer containing 50 mM Tris, 10 mM MgCl$_2$, 2 mM EGTA, pH 7.0 at 22° C. using a Polytron (Brinkmann Instruments, Westbury, N.Y.; setting 6) for 20 s. The homogenate was centrifuged at 48,000×g for 10 min at 4° C. The supernatant was discarded, and the pellet was re-homogenized in the same volume of buffer and centrifuged at 48,000×g for 10 min at 4° C. The resulting pellet was resuspended in the above buffer to a final concentration of 20–40 mg original wet weight/ml and used in the assays described below.

Protein determinations were performed according to the method of Lowry [Lowry et al., *J. Biol. Chem.* 193:265 (1951)] using bovine serum albumin as a standard.

CRF Receptor Binding: Receptor binding assays were carried out essentially as described by E. B. De Souza, *J. Neurosci.* 7:88 (1987).

Saturation Curve Analysis

In saturation studies, 100 μl $^{125}$I-ovineCRF (50 pM–10 nM final concentration), 100 μl of assay buffer (with or without 1 mM r/hCRF final concentration, to define the non-specific binding) and 100 μl of membrane suspension (as described above) were added in sequence to 1.5 ml polypropylene microfuge tubes for a final volume of 300 μl. All assays were carried out at equilibrium for 2 h at 22° C. as described by E. B. De Souza, *J. Neurosci.* 7:88 (1987). The reaction was terminated by centrifugation of the tubes in a Beckman microfuge for 5 min at 12,000×g. Aliquots of the supernatant were collected to determine the "free" radioligand concentration. The remaining supernatant was aspirated and the pellets washed gently with ice-cold PBS plus 0.01% Triton X-100, centrifuged again and monitored for bound radioactivity as described above. Data from saturation curves were analyzed using the non-linear least-squares curve-fitting program LIGAND [P. J. Munson and D. Rodbard, *Anal. Biochem.* 107:220 (1980)]. This program has the distinct advantage of fitting the raw experimental data on an untransformed coordinate system where errors are most likely to be normally distributed and uncorrelated with the independent variable. LIGAND does not expect the non-specific binding to be defined arbitrarily by the investigator, rather it estimates the value as an independent variable from the entire data set. The parameters for the affinity constants ($K_D$) and receptor densities ($B_{max}$) are also provided along with statistics on the general "fit" of the estimated parameters to the raw data. This program also offers the versatility of analyzing multiple curves simultaneously, thus improving the reliability of the data analysis and hence the validity of the final estimated parameters for any saturation experiment.

Competition Curve Analysis

In competition studies, 100 μl [$^{125}$I] ovine CRF ([$^{125}$I] oCRF; final concentration 200–300 pM) was incubated along with 100 μl buffer (in the presence of varying concentrations of competing ligands, typically 1 pM to 10 mM) and 100 μl of membrane suspension as prepared above to give a total reaction volume of 300 μl. The reaction was initiated by the addition of membrane homogenates, allowed to proceed to equilibrium for 2 h at 22° C. and was terminated by centrifugation (12,000×g) in a Beckman microfuge to separate the bound radioligand from free radioligand. The resulting pellets were surface washed twice by centrifugation with 1 ml of ice-cold phosphate buffered saline and 0.01% Triton X-100, the supernatants discarded and the pellets monitored for radioactivity at approximately 80% efficiency. The level of non-specific binding was defined in the presence of 1 μM unlabeled rat/humanCRF (r/hCRF). Data from competition curves were analyzed by the program LIGAND. For each competion curve, estimates of the affinity of the radiolabeled ligand for the CRF receptor ([$^{125}$I]CRF) were obtained in independent saturation experiments (as described above) and these estimates were constrained during the analysis of the apparent inhibitory constants ($K_i$) for the peptides tested. Routinely, the data were analyzed using a one- and two-site model comparing the "goodness of fit" between the models in order to accurately determine the Ki. Statistical analyses provided by LIGAND allowed the determination of whether a single-site or multiple-site model should be used. For both peptides (α-helical CRF$_{9-41}$ and d-PheCRF$_{12-41}$), as well as for all compounds of this invention, data were fit significantly to a single site model; a two-site model was either not possible or did not significantly improve the fit of the estimated parameters to the data.

The results of the in vitro testing of the compounds of the invention of Formula I demonstrated binding affinities for the CRF receptor, expressed as a $K_i$ value, in the range of 2–5000 nM It was found, for a representative number of compounds of the invention, that either form of the compound, be it the free-base or the hydrochloride salt, produced essentially the same inhibition value in the binding assay.

Inhibition of CRF-Stimulated Adenylate Cyclase Activity

Inhibition of CRF-stimulated adenylate cyclase activity was performed as described by G. Battaglia et al. *Synapse* 1:572 (1987). Briefly, assays were carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range 10$^9$ to 10$^{-6m}$) and 0.8 mg original wet weight tissue (approximately 40–60 mg protein). Reactions were initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Representative compounds of this invention were found to be active in this assay.

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from $10^{-10}$–$10^{-5}$ M), 100 μl of $^{125}$I-o-CRF (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND, which provides Ki values for inhibition which are then used to assess biological activity.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be tested in any species of rodent or small mammal. Disclosure of the assays herein is not intended to limit the enablement of the invention. The foregoing tests results demonstrate that compounds of this invention have utility in the treatment of imbalances associated abnormal with levels of corticotropin releasing factor in patients suffering from depression, affective disorders, and/or anxiety. Moreover such compounds would be useful in the treatment of affective disorders, anxiety, depression, post-traumatic stress disorders, eating disorders, supranuclear palsey, irritable bowl syndrome, immune supression, Alzheimer's disease, gastrointestinal diseases, anorexia nervosa, drug and alcohol withdrawal symptoms, drug addiction, inflammatory disorders, or fertility problems.

Compounds of this invention can be administered to treat said abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring of flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption. The compounds of this invention may also be used as reagents or standards in the biochemical study of neurological function, dysfunction, and disease.

What is claimed is:

1. A compound of formula (I):

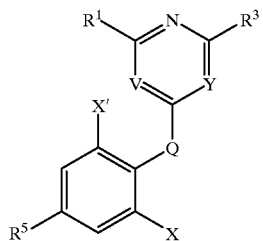

(I)

or a pharmaceutically acceptable salt thereof, wherein:

Q=O, S(O)n;

$R^1$ is $C_1$–$C_4$-alkyl, $C_1$–$C_4$-alkenyl, $C_1$–$C_4$-alkynyl, $C_1$–$C_2$ haloalkyl, halogen, $NR^6R^7$, $SR^8$, CN;

$R^3$ is $C_1$–$C_8$ alkyl, $C_1$–$C_2$ haloalkyl, halogen, $NR^6R^7$, $OR^8$, $SR^8$, $(CH_2)_kNR^6R^7$, $(CH_2)_kOR^8$, $CH(CHR^{16}CHR^{16}OR^8)_2$, $CH(CN)$aryl, $CH(CN)_2$, $CHR^{16}(CHR^{16})_pOR^8$, $(CHR^{16})_p$aryl wherein the aryl group is substituted with 1–3 $R^{18}$, $(CHR^{16})_p$heteroaryl wherein the heteroaryl group is substituted with 1–3 $R^{18}$, or $R^3$ is 1-tetrahydroquinolinyl, 2-tetrahydroisoquinolinyl, phenyl or heteroaryl substituted with 1–3 $S(O)z$—$(C_1$–$C_6)$alkyl;

X and X' are independently selected at each occurrence from the group consisting of alkyl, halogen, $S(O)_nR^8$, $OR^8$, halomethyl, $NR^{14}R^{15}$, CN;

$R^5$ is H, halo, $C_1$–$C_6$ alkyl, $C_2$–$C_6$ alkenyl, $C_1$–$C_3$ haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_4$–$C_6$ cycloalkenyl, CN;

$R^6$ and $R^7$ are independently selected at each occurrence from the group consisting of: hydrogen, $C_1$–$C_6$ alkyl, $C_3$–$C_{10}$ cycloalkyl, $C_3$–$C_{10}$ cycloalkylalkyl, $CH(R^{16})(CHR^{16})_pOR^8$, $(CHR^{16})_pOR^8$, —$(C_1$–$C_6$ alkyl)-aryl, heteroaryl, —$(C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, amino, $NHC(=O)(C_1$–$C_6$ alkyl), $NH(C_1$–$C_6$ alkyl), $N(C_1$–$C_6$ alkyl)$_2$, nitro, $CO_2(C_1$–$C_6$ alkyl), cyano, $S(O)_z$—$(C_1$–$C_6$-alkyl), or $R^6$ and $R^7$ can be taken together to form —$(CH_2)_qA(CH_2)_r$—, optionally substituted with 0–3 $R^{17}$, or when considered with the commonly attached nitrogen, $R^6$ and $R^7$ can be taken together to form a heterocycle, said heterocycle being substituted on carbon with 1–3 groups consisting of: hydrogen, $C_1$–$C_6$ alkyl, $(C_1$–$C_6)$alkyl$(C_1$–$C_4)$alkoxy, hydroxy, or $C_1$–$C_6$ alkoxy;

A is $CH_2$, O, $S(O)_n$, $N(C(=O)R^{24})$, $N(R^{19})$, $C(H)(NR^{14}R^{15})$, $C(H)(OR^{20})$, $C(H)(C(=O)R^{21})$, $N(S(O)_nR^{21})$;

$R^8$ is hydrogen, $C_1$–$C_6$ alkyl, $C_3$–$C_6$ cycloalkyl, $(CH_2)_tR^{22}$, $C_3$–$C_{10}$ cycloalkyl, cycloalkylalkyl, —$(C_1$–$C_6$ alkyl)-aryl, heteroaryl, —$(C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, amino, $NHC(=O)(C_1$–$C_6$ alkyl), $NH(C_1$–$C_6$ alkyl), $N(C_1$–$C_6$ alkyl)$_2$, nitro, $CO_2(C_1$–$C_6$ alkyl), cyano; $S(O)_z(C_1$–$C_6$-alkyl);

$R^{14}$ and $R^{15}$ are independently hydrogen, $C_1$–$C_6$ alkyl, $C_3$–$C_6$ cycloalkyl, $(CH_2)_tR^{22}$, aryl substituted with 0–3 $R^{18}$;

$R^{16}$ is hydrogen or $C_1$–$C_4$ alkyl;

$R^{17}$ is hydrogen, $C_1$–$C_4$ alkyl, $C_1$–$C_4$ alkoxy, halo, $OR^{23}$, $SR^{23}$, $NR^{23}R^{24}$, $(C_1$–$C_6)$ alkyl, $(C_1$–$C_4)$ alkoxy;

$R^{18}$ is hydrogen, $C_1$–$C_4$ alkyl, $C_1$–$C_2$ haloalkyl, $C_1$–$C_4$ alkoxy, $C(=O)R^{24}$, $NO_2$, halogen or cyano;

$R^{19}$ is $C_1$–$C_6$ alkyl, $C_3$–$C_6$ cycloalkyl, $(CH_2)_wR^{22}$, aryl substituted with 0–3 $R^{18}$;

$R^{20}$ is hydrogen, $C(=O)R^{22}$, $C_1$–$C_4$ alkyl, $C_2$–$C_4$ alkenyl;

$R^{21}$ is hydrogen, $C_1$–$C_4$ alkoxy, $NR^{23}R^{24}$, hydroxyl or $C_1$–$C_4$ alkyl;

$R^{22}$ is cyano, $OR^{24}$, $SR^{24}$, $NR^{23}R^{24}$, $C_3$–$C_6$ cycloalkyl;

$R^{23}$ and $R^{24}$ are independently selected at each occurrence from hydrogen or $C_1$–$C_4$ alkyl;

k is 1–4;

n is independently selected at each occurrence from 0–2;

p is 0–3;

q is 0–3;

r is 1–4;

t is independently selected at each occurrence from 1–6;

z=0–3; and w=1–6, wherein aryl is selected from the group consisting of phenyl, biphenyl and napthyl, wherein heteroaryl is selected from the group consisting of 2-, or 3-, or 4-pyridyl, 2- or 3-furyl, 2- or 3-benzofuranyl, 2-, or 3-thiophenyl, 2- or 3-benzo[b]thiophenyl, 2-, or 3-, or 4-quinolinyl, 1-, or 3-, or 4-isoquinolinyl, 2- or 3-pyrrolyl, 1- or 2- or 3-indolyl, 2-, or 4-, or 5-oxazolyl, 2-benzoxazolyl, 2- or 4- or 5-imidazolyl, 1- or 2-benzimidazolyl, 2- or 4- or 5-thiazolyl, 2-benzothiazolyl, 3- or 4- or 5-isoxazolyl, 3- or 4- or 5-pyrazolyl, 3- or 4- or 5-isothiazolyl, 3- or 4-pyridazinyl, 2- or 4- or 5-pyrimidinyl, 2-pyrazinyl, 2-triazinyl, 3- or 4-cinnolinyl, 1-phthalazinyl, 2- or 4-quinazolinyl, or 2-quinoxalinyl ring, and wherein heterocyclic is selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a,H-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclideinyl, morpholinyl or oxazolidinyl;

with the proviso that $R^1$ and $R^3$ are not the same.

2. A compound of claim 1 wherein:

$R^3$ is $C_1$–$C_4$ alkyl, $C_1$–$C_2$ haloalkyl, $NR^6R^7$, $OR^8$, $CH(CHR^{16}CHR^{16}OR^8)_2$, $CH(CN)aryl$, $CH(CN)_2$, $CHR^{16}(CHR^{16})_pOR^8$, $(CHR^{16})_p aryl$ wherein the aryl group is substituted with 1–3 $R^{18}$, $(CHR^{16})_p heteroaryl$ wherein the heteroaryl group is substituted with 1–3 $R^{18}$, or $R^3$ is 1-tetrahydroquinolinyl, 2-tetrahydroisoquinolinyl, phenyl or heteroaryl substituted with 1–3 $S(O)z$—$(C_1$–$C_6)alkyl$;

$R^6$ and $R^7$ are independently selected at each occurrence from the group consisting of: hydrogen, $C_1$–$C_6$ alkyl, $C_3$–$C_{10}$ cycloalkyl, $C_3$–$C_{10}$ cycloalkylalkyl, $C_1$–$C_6$ alkoxy, $(CHR^{16})_pOR^8$, —$(C_1$–$C_6$ alkyl)-aryl, heteroaryl, —$(C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, $NHC(=O)(C_1$–$C_6$ alkyl), $NH(C_1$–$C_6$ alkyl), $N(C_1$–$C_6$ alkyl)$_2$, $CO_2(C_1$–$C_6$ alkyl), cyano, or $R^6$ and $R^7$ can be taken together to form —$(CH_2)_qA(CH_2)_r$—, optionally substituted with 0–3 $R^{17}$, or when considered with the commonly attached nitrogen, $R_6$ and $R^7$ can be taken together to form a heterocycle, said heterocycle being substituted on carbon with 1–3 groups consisting of: hydrogen, $C_1$–$C_6$ alkyl, $(C_1$–$C_6)alkyl(C_1$–$C_4)alkoxy$, hydroxy, or $C_1$–$C_6$ alkoxy;

$R^8$ is hydrogen, $C_1$–$C_6$ alkyl, $C_3$–$C_6$ cycloalkyl, $(CH_2)_rR^{22}$, $C_3$–$C_{10}$ cycloalkyl, cycloalkylalkyl, —$(C_1$–$C_6$ alkyl)-aryl, or hetero-aryl optionally substituted with 1–3 groups selected from the following: hydrogen, halogen, $C_1$–$C_6$ alkyl, $C_1$–$C_6$ alkoxy, $NHC(=O)(C_1$–$C_6$ alkyl), $NH(C_1$–$C_6$ alkyl), $N(C_1$–$C_6$ alkyl)$_2$, $CO_2(C_1$–$C_6$ alkyl);

$R^{14}$ and $R^{15}$ are independently hydrogen, $C_1$–$C_6$ alkyl, $C_3$–$C_6$ cycloalkyl;

$R^{17}$ is hydrogen, $C_1$–$C_4$ alkyl, $C_1$–$C_4$ alkoxy, $(C_1$–$C_6)$ alkyl, $(C_1$–$C_4)$ alkoxy;

$R^{18}$ is hydrogen, $C_1$–$C_4$ alkyl, $C_1$–$C_2$ haloalkyl, $C_1$–$C_4$ alkoxy, or cyano;

$R^{19}$ is $C_1$–$C_6$ alkyl, $C_3$–$C_6$ cycloalkyl, aryl substituted with 0–3 $R^{18}$;

$R^{22}$ is cyano, $OR^{24}$, $SR^{24}$, $NR^{23}R^{24}$, $C_3$–$C_6$ alkyl or cycloalkyl;

$R^{23}$ and $R^{24}$ are independently selected at each occurrence from hydrogen, $C_1$–$C_4$ alkyl;

t is independently selected at each occurrence from 1–3; and w=1–3.

3. A method of treating anxiety or depression in mammals comprising administering to the mammal a therapeutically effective amount of a compound of claim 1.

4. A method of treating anxiety or depression in mammals comprising administering to the mammal a therapeutically effective amount of a compound of claim 1.

5. A compound of claim 1 wherein:

$R^1$ is $C_1$–$C_2$ alkyl, halide, $NR^6R^7$, $OR^8$;

$R^3$ is $C_1$–$C_4$ alkyl, $C_1$–$C_2$ haloalkyl, $NR^6R^7$, $OR^8$, $(CH_2)_kNR^6R^7$, $(CH_2)_kOR^8$;

Y is N;

X and X' are independently selected at each occurrence from the group consisting of methyl, hydrogen, Cl, Br, I, $OR^8$, $NR^{14}R^{15}$, CN, $S(O)nR^8$;

$R^5$ is H, halo, $C_1$–$C_6$ alkyl, $C_1$–$C_3$ haloalkyl, $C_1$–$C_6$ alkoxy, $(CHR^{16})_pOR^8$, $(CHR^{16})_pNR^{14}R^{15}$, $C_4$–$C_6$ cycloalkyl;

$R^6$ and $R^7$ are independently selected at each occurrence from the group consisting of: $C_1$–$C_6$ alkyl, $(CHR^{16})_pR^8$; or can be taken together to form —$(CH_2)_qA(CH_2)_r$—, optionally substituted with $CH_2OCH_3$;

A is $CH_2$, O, $S(O)_n$, $N(C(=O)R^{18})$, $N(R^{19})$, $C(H)(OR^{20})$;

$R^8$ is hydrogen, $C_1$–$C_6$ alkyl, $C_3$–$C_6$ cycloalkyl, $(CH_2)_t R^{22}$;

$R^9$ is hydroxy, $C_1$–$C_4$ alkyl, or methoxy;

$R^{13}$ is $OR^{19}$, $SR^{19}$, $NR^{23}R^{24}$, $C_3$–$C_6$ cycloalkyl;

$R^{14}$ and $R^{15}$ are independently is hydrogen, $C_1$–$C_2$ alkyl, $C_3$–$C_6$ cycloalkyl;

$R^{16}$ is hydrogen;

$R^{18}$ is hydrogen, $C_1$–$C_4$ alkyl, $C_1$–$C_2$ haloalkyl, $C_1$–$C_4$ alkoxy, $C(=O)R^{24}$, or cyano;

$R^{19}$ is $C_1$–$C_3$ alkyl;

$R^{20}$ is hydrogen, $C_1$–$C_2$ alkyl or $C_2$–$C_3$ alkenyl;

$R^{22}$ is $OR^{24}$;

$R^{23}$ and $R^{24}$ are independently selected at each occurrence from hydrogen or $C_1$–$C_2$ alkyl;

k is 1–3;

m is 1–4;

n is independently selected at each occurrence from 0–2;

p is 0–2;

q is 0–2;

r is 1–2;

t is independently selected at each occurrence from 1–3;

w is 1–3.

6. A compound of claim 1 selected from the group:

a) 2-[2-Bromo-6-methoxy-4(1-methylethenyl)phenoxy]-4-methyl-6-(4-morpholinyl)-1,3,5-triazine;

b) 2-[2-Bromo-6-methoxy-4(1-methylethenyl)phenoxy]-4-methyl-6-(bis(2-methoxyethyl)amino)-1,3,5-triazine;
c) 2-[2-Bromo-6-methoxy-4(1-methylethenyl)phenoxy]-4-methyl-6-(N-propyl-N-cyclopropylmethylamino)-1,3,5-triazine;
d) 2-[2-Bromo-6-methoxy-4(1-methylethenyl)phenoxy]-4-methyl-6-(1-homopiperidinyl)-1,3,5-triazine;
e) 2-[2-Bromo-6-methoxy-4(1-methylethenyl)phenoxy]-4-methyl-6-(diethylamino)-1,3,5-triazine;
f) 2-[2-Bromo-6-methoxy-4(1-methylethenyl)phenoxy]-4-methyl-6-(N-butyl-N-ethylamino)-1,3,5-triazine;
g) 2-[2-Bromo-6-methoxy-4(1-methylethenyl)phenoxy]-4-methyl-6-(4-thiomorpholinyl)-1,3,5-triazine;
h) 2-[2-Bromo-6-methoxy-4(1-methylethenyl)phenoxy]-4-methyl-6-(2-(1-methoxybutyl)amino)-1,3,5-triazine;
i) 2-[2-Bromo-6-methoxy-4(1-methylethenyl)phenoxy]-4-methyl-6-(1-piperidinyl)-1,3,5-triazine;
j) 2-[2-Bromo-6-methoxy-4(1-methylethenyl)phenoxy]-4-methyl-6-(1-(1,2,3,4-tetrahydroquinolinyl))-1,3,5-triazine;
k) 2-(2-Bromo-6-methoxy-4(1-methylethenyl)phenoxyl-4-methyl-6-(1-pyrrolidinyl)-1,3,5-triazine; and
l) 2-[2-Bromo-6-methoxy-4(1-methylethenyl)phenoxy]-4-methyl-6-(1-(2-ethylpieridinyl))-1,3,5-triazine.

7. A method of treating anxiety or depression in mammals comprising administering to the mammal a therapeutically effective amount of a compound of claim 5.

8. A method of treating anxiety or depression in mammals comprising administering to the mammal a therapeutically effective amount of a compound of claim 6.

9. A pharmaceutical composition comprising a pharmaceutically acceptable carrier and a therapeutically effective amount of a compound of claim 5.

10. A pharmaceutical composition comprising a pharmaceutically acceptable carrier and a therapeutically effective amount of a compound of claim 6.

11. A compound of claim 1 selected from the group:
a) 2-[2-Bromo-6-methoxy-4(1-methylethenyl)phenoxy]-4 methyl-6-(2-(1,2,3,4-tetrahydroisoquinolinyl))-1,3,5-triazine;
b) 2-[2-Bromo-6-methoxy-4(1-methylethenyl)phenoxy]-4-methyl-6-(1-(1,3,5,6-tetrahyropiperidinyl)-1,3,5-triazine;
c) 2-[2-Bromo-6-methoxy-4(1-methylethenyl)phenoxy]-4-methyl-6-(1-(2-trifluoromethylphenyl))-1,3,5-triazine;
d) 2-[2-Bromo-6-methoxy-4(1-methylethyl)phenoxy]-4-methyl-6-(4-morpholinyl)-1,3,5-triazine;
e) 2-[2-Bromo-6-methoxy-4(1-methylethyl)phenoxy]-4-methyl-6-(bis(2-methoxyethyl)amino)-1,3,5-triazine;
f) 2-[2-Bromo-6-methoxy-4(1-methylethyl)phenoxy]-4-methyl-6-(N-propyl-N-cyclopropylmethylamino)-1,3,5-triazine;
g) 2-[2-Bromo-6-methoxy-4(1-methylethyl)phenoxy]-4-methyl-6-(1-homopiperidinyl)-1,3,5-triazine;
h) 2-[2-Bromo-6-methoxy-4(1-methylethyl)phenoxy]-4-methyl-6-(N-butyl-N-ethylamino)-1,3,5-triazine;
i) 2-[2-Bromo-6-methoxy-4(1-methylethyl)phenoxy]-4-methyl-6-(4-thiomorpholinyl)-1,3,5-triazine;
j) 1-[3-Bromo-5-methoxy-4-[[4-methyl-6-(4-morpholinyl)-1,3,5-triazinyl-2-yl]oxy]phenyl]ethanone;
k) 1-[3-Bromo-5-methoxy-4-[[4-methyl-6-(bis(2-methoxyethyl)amino)-1,3,5-triazinyl-2-yl]oxy]phenyl]ethanone;
l) 1-[3-Bromo-5-methoxy-4-[[4-methyl-6-(4-thiomorpholinyl)-1,3,5-triazinyl-2-yl]oxy]phenyl]ethanone; and
m) 1-[3-Bromo-5-methoxy-4-[[4-methyl-6-diethylamino)-1,3,5-triazinyl-2-yl]oxy]phenyl]ethanone.

12. A compound of claim 1 selected from the group:
a) 1-[3-Bromo-5-methoxy-4-[[4-methyl-6-(1-piperidinyl)-1,3,5-triazinyl-2-yl]oxy]phenyl]ethanone;
b) 3-Bromo-4-[[6-methyl-4(bis(2-methoxyethyl)amino)-1,3,5-triazin-2-yl]oxy]-5-methoxy-alpha,alpha-dimethylbenzenemethanol;
c) 3-Bromo-4-[[6-methyl-4(N-propyl-N-cyclopropylmethylamino)-1,3,5-triazin-2-yl]oxy]-5-methoxy-alpha,alpha-dimethylbenzenemethanol;
d) 3-Bromo-4-[[6-methyl-4(2-(1-methoxybutyl)amino)-1,3,5-triazin-2-yl]oxy]-5-methoxy-alpha,alpha-dimethylbenzenemethanol;
e) 3-Bromo-4-[[6-methyl-4(4-thiomormopholinyl)-1,3,5-triazin-2-yl]oxy]-5-methoxy-alpha,alpha-dimethylbenzenemethanol;
f) 3-Bromo-4-[[6-methyl-4(1-piperidinyl)-1,3,5-triazin-2-yl]oxy]-5-methoxy-alpha,alpha-dimethylbenzenemethanol;
g) 3-Bromo-4-[[6-methyl-4(1-homopiperidinyl)-1,3,5-triazin-2-yl]oxy]-5-methoxy-alpha,alpha-dimethylbenzenemethanol;
h) 3-Bromo-4-[[6-methyl-4(1-(2-trifluoromethylphenyl))-1,3,5-triazin-2-yl]oxy]-5-methoxy-alpha,alpha-dimethylbenzenemethanol;
i) 2-(2,4,6-Triodophenoxy)-4-methyl-6-(4-morpholinyl)-1,3,5-triazine;
j) 2-(2,4,6-Trichlorophenoxy)-4-methyl-6-(4-morpholinyl)-1,3,5-triazine;
k) 2-(2-chloro-4,6-Dimethoxyphenoxy)-4-methyl-6-(4-morpholinyl)-1,3,5-triazine; and
l) 2-[(2,6-Dibromo-4-(1-methylethyl))phenoxy]-4-methyl-6-(N-ethyl-N-butylamino)-1,3,5-triazine; and
m) 2-[(2,6-Dibromo-4-(1-methylethyl))phenoxy]-4-methyl-6-(bis(2-methoxyethyl)amino)-1,3,5-triazine.

13. A pharmaceutical composition comprising a pharmaceutically acceptable carrier and a therapeutically effective amount of a compound of claim 11.

14. A pharmaceutical composition comprising a pharmaceutically acceptable carrier and a therapeutically effective amount of a compound of claim 12.

15. A compound of formula (I):

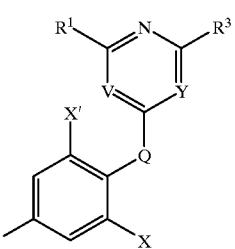

(I)

or a pharmaceutically acceptable salt thereof, wherein:

Q=O, S(O)n;

$R^1$ is $OR^8$;

$R^3$ is $C_1$–$C_8$ alkyl, $C_1$–$C_2$ haloalkyl, halogen, $NR^6R^7$, $OR^8$, $SR^8$, $(CH_2)_kNR^6R^7$, $(CH_2)_kOR^8$, $CH(CHR^{16}CHR^{16}OR^8)_2$, $CH(CN)aryl$, $CH(CN)_2$, $CHR^{16}(CHR^{16})_pOR^8$, $(CHR^{16})_paryl$ wherein the aryl group is substituted with 1–3 $R^{18}$, $(CHR^{16})_pheteroaryl$ wherein the heteroaryl group is substituted with 1–3 $R^{18}$, or $R^3$ is 1-tetrahydroquinolinyl, 2-tetrahydroisoquinolinyl, phenyl or heteroaryl substituted with 1–3 $S(O)z$—$(C_1$–$C_6)alkyl$;

X and X' are independently selected at each occurrence from the group consisting of alkyl, halogen, $S(O)_nR^8$, $OR^8$, halomethyl, $NR^{14}R^{15}$, CN;

$R^5$ is H, halo, $C_1$–$C_6$ alkyl, $C_2$–$C_6$ alkenyl, $C_1$–$C_3$ haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_4$–$C_6$ cycloalkenyl, CN;

$R^6$ and $R^7$ are independently selected at each occurrence from the group consisting of: hydrogen, $C_1$–$C_6$ alkyl, $C_3$–$C_{10}$ cycloalkyl, $C_3$–$C_{10}$ cycloalkylalkyl, $CH(R^{16})$ (CHR$^{16}$)$_p$OR$^8$, (CHR$^{16}$)$_p$OR$^8$, —(C$_1$–C$_6$ alkyl)-aryl, heteroaryl, —(C$_1$–C$_6$ alkyl)-heteroaryl or aryl optionally substituted with 1–3 groups selected from the following: hydrogen, halogen, C$_1$–C$_6$ alkyl, C$_1$–C$_6$ alkoxy, amino, NHC(=O)(C$_1$–C$_6$ alkyl), NH(C$_1$–C$_6$ alkyl), N(C$_1$–C$_6$ alkyl)$_2$, nitro, CO$_2$(C$_1$–C$_6$ alkyl), cyano, S(O)$_{z}$(C$_1$–C$_6$-alkyl), or R$^6$ and R$^7$ can be taken together to form —(CH$_2$)$_q$A(CH$_2$)r—, optionally substituted with 0–3 R$^{17}$, or when considered with the commonly attached nitrogen, R$^6$ and R$^7$ can be taken together to form a heterocycle, said heterocycle being substituted on carbon with 1–3 groups consisting of: hydrogen, C$_1$–C$_6$ alkyl, (C$_1$–C$_6$) alkyl(C$_1$–C$_4$)alkoxy, hydroxy, or C$_1$–C$_6$ alkoxy;

A is CH$_2$, O, S(O)$_n$, N(C(=O)R$^{24}$), N(R$^{19}$), C(H)(NR$^{14}$R$^{15}$), C(H)(OR$^{20}$), C(H)(C(=O)R$^{21}$), N(S(O)$_n$R$^{21}$);

R$^8$ is hydrogen, C$_1$–C$_6$ alkyl, C$_3$–C$_6$ cycloalkyl, (CH$_2$)$_t$R$^{22}$, C$_3$–C$_{10}$ cycloalkyl, cycloalkylalkyl, —(C$_1$–C$_6$ alkyl)-aryl, heteroaryl, —(C$_1$–C$_6$ alkyl)-heteroaryl or aryl optionally substituted with 1–3 groups selected from the following: amino, NHC(=O) (C$_1$–C$_6$ alkyl), NH(C$_1$–C$_6$ alkyl), N(C$_1$–C$_6$ alkyl)$_2$, CO$_2$(C$_1$–C$_6$ alkyl), cyano; S(O)$_z$(C$_1$–C$_6$-alkyl);

R$^{14}$ and R$^{15}$ are independently hydrogen, C$_1$–C$_6$ alkyl, C$_3$–C$_6$ cycloalkyl, (CH$_2$)$_t$R$^{22}$, aryl substituted with 0–3 R$^{18}$;

R$^{16}$ is hydrogen or C$_1$–C$_4$ alkyl;

R$^{17}$ is hydrogen, C$_{1-4}$ alkyl, C$_{1-4}$ alkoxy, halo, OR$^{23}$, SR$^{23}$, NR$^{23}$R$^{24}$, (C$_1$–C$_6$) alkyl, (C$_1$–C$_4$) alkoxy;

R$^{19}$ is C$_1$–C$_6$ alkyl, C$_3$–C$_6$ cycloalkyl, (CH$_2$)$_w$R$^{22}$, aryl substituted with 0–3 R$^{18}$;

R$^{20}$ is hydrogen, C(=O)R$^{22}$, C$_1$–C$_4$ alkyl, C$_2$–C$_4$ alkenyl;

R$^{21}$ is hydrogen, C$_1$–C$_4$ alkoxy, NR$^{23}$R$^{24}$, hydroxyl or C$_1$–C$_4$ alkyl;

R$^{22}$ is cyano, OR$^{24}$, SR$^{24}$, NR$^{23}$R$^{24}$, C$_3$–C$_6$ cycloalkyl;

R$^{23}$ and R$^{24}$ are independently selected at each occurrence from hydrogen or C$_1$–C$_4$ alkyl;

k is 1–4;

n is independently selected at each occurrence from 0–2;

p is 0–3;

q is 0–3;

r is 1–4;

t is independently selected at each occurrence from 1–6;

z=0–3; and w=1–6, wherein aryl is selected from the group consisting of phenyl, biphenyl and napthyl, wherein heteroaryl is selected from the group consisting of 2-, or 3-, or 4-pyridyl, 2- or 3-furyl, 2- or 3-benzofuranyl, 2-, or 3-thiophenyl, 2- or 3-benzo[b]thiophenyl, 2-, or 3-, or 4-quinolinyl, 1-, or 3-, or 4-isoquinolinyl, 2- or 3-pyrrolyl, 1- or 2- or 3- indolyl, 2-, or 4-, or 5-oxazolyl, 2-benzoxazolyl, 2- or 4- or 5-imidazolyl, 1- or 2-benzimidazolyl, 2- or 4- or 5-thiazolyl, 2-benzothiazolyl, 3- or 4- or 5-isoxazolyl, 3- or 4- or 5-pyrazolyl, 3- or 4- or 5-isothiazolyl, 3- or 4-pyridazinyl, 2- or 4- or 5-pyrimidinyl, 2-pyrazinyl, 2-triazinyl, 3- or 4-cinnolinyl, 1-phthalazinyl, 2- or 4-quinazolinyl, or 2-quinoxalinyl ring, and wherein heterocyclic is selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a,H-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclideinyl, morpholinyl or oxazolidinyl;

with the proviso that R$^1$ and R$^3$ are not the same.

16. A compound of claim 15 wherein:

Q=O;

R$^1$ is OR$^8$;

R$^3$ is OR$^8$;

X and X' are independently selected at each occurrence from the group consisting of alkyl, halogen, S(O)$_n$R$^8$, OR$^8$, halomethyl, NR$^{14}$R$^{15}$, CN;

R$^5$ is H, halo, C$_1$–C$_6$ alkyl, C$_2$–C$_6$ alkenyl, C$_1$–C$_3$ haloalkyl, C$_1$–C$_6$ alkoxy, (CHR$^{16}$)$_p$OR$^8$, (CHR$^{16}$)$_p$S(O)$_n$R$^8$, (CHR$^{16}$)$_p$NR$^{14}$R$^{15}$, C$_3$–C$_6$ cycloalkyl, C$_4$–C$_6$ cycloalkenyl, CN;

R$^8$ is aryl optionally substituted with 1–3 groups selected from the following: amino, NHC(=O)(C$_1$–C$_6$ alkyl), NH(C$_1$–C$_6$ alkyl), N(C$_1$–C$_6$ alkyl)$_2$, CO$_2$(C$_1$–C$_6$ alkyl), cyano; S(O)$_z$(C$_1$–C$_6$-alkyl);

R$^{14}$ and R$^{15}$ are independently hydrogen, C$_1$–C$_6$ alkyl, C$_3$–C$_6$ cycloalkyl, (CH$_2$)$_t$R$^{22}$, aryl substituted with 0–3 R$^{18}$;

R$^{16}$ is hydrogen or C$_1$–C$_4$ alkyl;

R$^{18}$ is hydrogen, C$_1$–C$_4$ alkyl, C$_1$–C$_2$ haloalkyl, C$_1$–C$_4$ alkoxy, C(=O)R$^{24}$, NO$_2$, halogen or cyano;

n is independently selected at each occurrence from 0–2;

p is 0–3;

t is independently selected at each occurrence from 1–6;

z=0–3; and wherein aryl is selected from the group consisting of phenyl, biphenyl and napthyl, with the proviso that R$^1$ and R$^3$ are not the same.

17. A compound of formula (I):

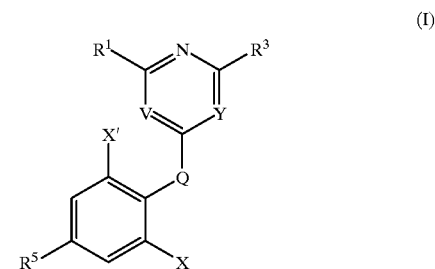

(I)

or a pharmaceutically acceptable salt thereof, wherein:

Q=S(O)n;

R$^1$ is C$_1$–C$_4$-alkyl, C$_1$–C$_4$-alkenyl, C$_1$–C$_4$-alkynyl, C$_1$–C$_2$ haloalkyl, halogen, NR$^6$R$^7$, OR$^8$, SR$^8$, CN;

$R^3$ is $C_1$–$C_8$ alkyl, $C_1$–$C_2$ haloalkyl, halogen, $NR^6R^7$, $OR^8$, $SR^8$, $(CH_2)_kNR^6R^7$, $(CH_2)_kOR^8$, $CH(CHR^{16}CHR^{16})_pOR^8)_2$, $CH(CN)aryl$, $CH(CN)_2$, $CHR^{16}(CHR^{16})_pOR^8$, $(CHR^{16})_p$aryl wherein the aryl group is substituted with 1–3 $R^{18}$, $(CHR^{16})_p$heteroaryl wherein the heteroaryl group is substituted with 1–3 $R^{18}$, or $R^3$ is 1-tetrahydroquinolinyl, 2-tetrahydroisoquinolinyl, phenyl or heteroaryl substituted with 1–3 S(O)z—($C_1$–$C_6$)alkyl;

X and X' are independently selected at each occurrence from the group consisting of alkyl, halogen, $S(O)_nR^8$, $OR^8$, halomethyl, $NR^{14}R^{15}$, CN;

$R^5$ is H, halo, $C_1$–$C_6$ alkyl, $C_2$–$C_6$ alkenyl, $C_1$–$C_3$ haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_4$–$C_6$ cycloalkenyl, CN;

$R^6$ and $R^7$ are independently selected at each occurrence from the group consisting of: hydrogen, $C_1$–$C_6$ alkyl, $C_3$–$C_{10}$ cycloalkyl, $C_3$–$C_{10}$ cycloalkylalkyl, $CH(R^{16})(CHR^{16})_pOR^8$, $(CHR^{16})_pOR^8$, —($C_1$–$C_6$ alkyl)-aryl, heteroaryl, —($C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), ($C_1$–$C_6$ alkyl)$_2$, nitro, $CO_2$($C_1$–$C_6$ alkyl), cyano, $S(O)_z$—N($C_1$–$C_6$-alkyl), or $R^6$ and $R^7$ can be taken together to form —$(CH_2)_qA(CH_2)_r$—, optionally substituted with 0–3 $R^{17}$, or when considered with the commonly attached nitrogen, $R^6$ and $R^7$ can be taken together to form a heterocycle, said heterocycle being substituted on carbon with 1–3 groups consisting of: hydrogen, $C_1$–$C_6$ alkyl, ($C_1$–$C_6$)alkyl($C_1$–$C_4$)alkoxy, hydroxy, or $C_1$–$C_6$ alkoxy;

A is $CH_2$, O, $S(O)_n$, $N(C(=O)R^{24})$, $N(R^{19})$, $C(H)(NR^{14}R^{15})$, $C(H)(OR^{20})$, $C(H)(C(=O)R^{21})$, $N(S(O)_nR^{21})$;

$R^8$ is hydrogen, $C_1$–$C_6$ alkyl, $C_3$–$C_6$ cycloalkyl, $(CH_2)_rR^{22}$, $C_3$–$C_{10}$ cycloalkyl, cycloalkylalkyl, —($C_1$–$C_6$ alkyl)-aryl, heteroaryl, —($C_1$–$C_6$ alkyl)-heteroaryl or aryl optionally substituted with 1–3 groups selected from the following: hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$ alkyl)$_2$, nitro, $CO_2$($C_1$–$C_6$ alkyl), cyano; $S(O)_z$($C_1$–$C_6$-alkyl);

$R^{14}$ and $R^{15}$ are independently hydrogen, $C_1$–$C_6$ alkyl, $C_3$–$C_6$ cycloalkyl, $(CH_2)_rR^{22}$, aryl substituted with 0–3 $R^{18}$;

$R^{16}$ is hydrogen or $C_1$–$C_4$ alkyl;

$R^{17}$ is hydrogen, $C_1$–$C_4$ alkyl, $C_1$–$C_4$ alkoxy, halo, $OR^{23}$, $SR^{23}$, $NR^{23}R^{24}$, ($C_1$–$C_6$) alkyl, ($C_1$–$C_4$) alkoxy;

$R^{18}$ is hydrogen, $C_1$–$C_4$ alkyl, $C_1$–$C_2$ haloalkyl, $C_1$–$C_4$ alkoxy, C(=O)$R^{24}$, $NO_2$, halogen or cyano;

$R^{19}$ is $C_1$–$C_6$ alkyl, $C_3$–$C_6$ cycloalkyl, $(CH_2)_wR^{22}$, aryl substituted with 0–3 $R^{18}$;

$R^{20}$ is hydrogen, C(=O)$R^{22}$, $C_1$–$C_4$ alkyl, $C_2$–$C_4$ alkenyl;

$R^{21}$ is hydrogen, $C_1$–$C_4$ alkoxy, $NR^{23}R^{24}$, hydroxyl or $C_1$–$C_4$ alkyl;

$R^{22}$ is cyano, $OR^{24}$, $SR^{24}$, $NR^{23}R^{24}$, $C_3$–$C_6$ cycloalkyl;

$R^{23}$ and $R^{24}$ are independently selected at each occurrence from hydrogen or $C_1$–$C_4$ alkyl;

k is 1–4;

n is independently selected at each occurrence from 0–2;

p is 0–3;

q is 0–3;

r is 1–4;

t is independently selected at each occurrence from 1–6;

z=0–3; and w=1–6, wherein aryl is selected from the group consisting of phenyl, biphenyl and napthyl, wherein heteroaryl is selected from the group consisting of 2-, or 3-, or 4-pyridyl, 2- or 3-furyl, 2- or 3-benzofuranyl, 2-, or 3-thiophenyl, 2- or 3-benzo[b]thiophenyl, 2-, or 3-, or 4-quinolinyl, 1-, or 3-, or 4-isoquinolinyl, 2- or 3-pyrrolyl, 1- or 2- or 3- indolyl, 2-, or 4-, or 5-oxazolyl, 2-benzoxazolyl, 2- or 4- or 5-imidazolyl, 1- or 2-benzimidazolyl, 2- or 4- or 5-thiazolyl, 2-benzothiazolyl, 3- or 4- or 5-isoxazolyl, 3- or 4- or 5-pyrazolyl, 3- or 4- or 5-isothiazolyl, 3- or 4-pyridazinyl, 2- or 4- or 5-pyrimidinyl, 2-pyrazinyl, 2-triazinyl, 3- or 4-cinnolinyl, 1-phthalazinyl, 2- or 4-quinazolinyl, or 2-quinoxalinyl ring, and wherein heterocyclic is selected from the group consisting of pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a,H-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclideinyl, morpholinyl or oxazolidinyl;

with the proviso that $R^1$ and $R^3$ are not the same.

18. A pharmaceutical composition comprising a pharmaceutically acceptable carrier and a therapeutically effective amount of a compound of claim 15.

19. A pharmaceutical composition comprising a pharmaceutically acceptable carrier and a therapeutically effective amount of a compound of claim 16.

20. A pharmaceutical composition comprising a pharmaceutically acceptable carrier and a therapeutically effective amount of a compound of claim 17.

* * * * *

UNITED STATES PATENT AND TRADEMARK OFFICE
CERTIFICATE OF CORRECTION

PATENT NO. : 6,326,368 B1
DATED : December 4, 2001
INVENTOR(S) : Robert John Chorvat et al.

It is certified that error appears in the above-identified patent and that said Letters Patent is hereby corrected as shown below:

Column 25,
Lines 38-50, formula (I) should appear as follows:

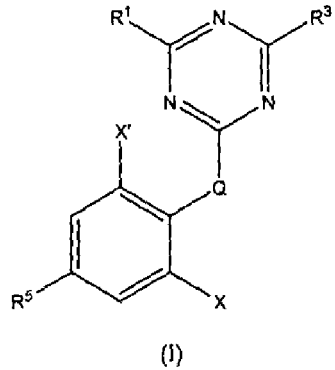

Column 28,
Line 22, the claim reference numeral "1" should read -- 2 --.

Column 30,
Lines 34-45, formula (I) should appear as follows:

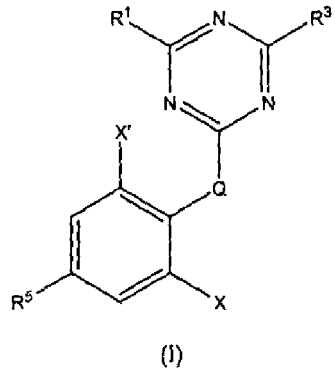

UNITED STATES PATENT AND TRADEMARK OFFICE
CERTIFICATE OF CORRECTION

PATENT NO. : 6,326,368 B1
DATED : December 4, 2001
INVENTOR(S) : Robert John Chorvat et al.

It is certified that error appears in the above-identified patent and that said Letters Patent is hereby corrected as shown below:

Column 32,
Lines 51-63, formula (I) should appear as follows:

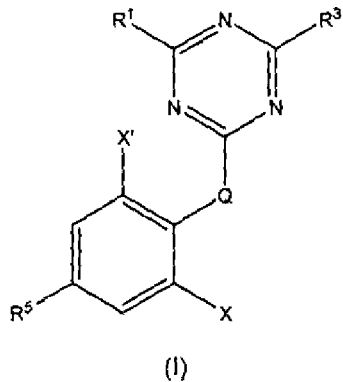

(I)

Signed and Sealed this

Twenty-fifth Day of January, 2005

JON W. DUDAS
*Director of the United States Patent and Trademark Office*